(12) United States Patent
Meerpoel et al.

(10) Patent No.: US 6,440,440 B1
(45) Date of Patent: Aug. 27, 2002

(54) BIOCIDAL BENZYLBIPHENYL DERIVATIVES

(76) Inventors: Lieven Meerpoel; Mark Arthur Josepha Van der Flaas; Louis Jozef Elisabeth Van Der Veken; Jan Heeres, all of Janssen Pharmaceutica N.V., Turnhoutseweg 30, Beerse, 2340 (BE)

( * ) Notice: Subject to any disclaimer, the term of this patent is extended or adjusted under 35 U.S.C. 154(b) by 0 days.

(21) Appl. No.: 09/647,015

(22) PCT Filed: Mar. 25, 1999

(86) PCT No.: PCT/EP99/02098
§ 371 (c)(1),
(2), (4) Date: Sep. 22, 2000

(87) PCT Pub. No.: WO99/51578
PCT Pub. Date: Oct. 14, 1999

(30) Foreign Application Priority Data

Feb. 4, 1998 (EP) .............................. 98201043

(51) Int. Cl.[7] ...................... A01N 43/40; C07D 40/104; C07C 211/10
(52) U.S. Cl. .................. 424/405; 546/191; 546/223; 546/229; 564/316; 504/248; 504/306
(58) Field of Search .................. 424/405; 546/191, 546/223, 229, 316; 504/248, 326

(56) References Cited

U.S. PATENT DOCUMENTS

| | | | |
|---|---|---|---|
| 4,251,655 A | 2/1981 | Scott et al. | 542/415 |
| 4,910,200 A | 3/1990 | Curtze et al. | 514/237.5 |

FOREIGN PATENT DOCUMENTS

| | | |
|---|---|---|
| GB | 788914 | 1/1958 |
| GB | 788915 | 1/1958 |

OTHER PUBLICATIONS

G.L. Regnier & R.J. Canevari, *Triphenylpropylpiperazine Derivatives as New Potent Analgetic Substances*, Journal of Medicinal Chemistry, 1972, vol. 15, No. 3, pp. 295–301.
L.P. Albro, R. Baltzly & A.P. Phillips, *Unsymmetrically Disubstituted Piperazines, II. Histamine Antagonists*, The Wellcome Research Laboratories, 1949, pp. 771–774.
Mann, N. et al., Arch. Pharm, pp:320–325, 1976.
Mann, N. et al., Arch Pharm. Vol. 306, pp. 671–678, 1973.

*Primary Examiner*—Charanjit Aulakh
(74) *Attorney, Agent, or Firm*—Ellen Ciambrone Coletti

(57) ABSTRACT

This invention concerns compounds of formula.

(I)

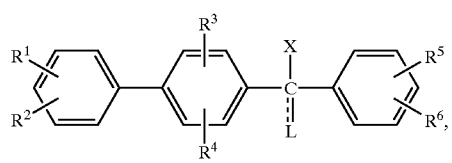

stereochemically isomeric forms thereof, acid or base addition salts thereof, N-oxides thereof, or quaternary ammonium derivatives thereof, wherein the dotted line is an optional bond; X is a direct bond when the dotted line represents a bond, or X is hydrogen or hydroxy, when the dotted line does not represent a bond; $R^1$, $R^2$, $R^5$ and $R^6$ are each independently selected from hydrogen, halo, hydroxy, $C_{1-4}$alkyl, $C_{1-4}$alkyloxy, —$SO_3H$, and the like; $R^3$ and $R^4$ are each independently selected from hydrogen, halo, hydroxy, $C_{1-4}$alkyl, $C_{1-4}$alkyloxy, nitro, amino, cyano, trifluoromethyl, or trifluoromethoxy; ===L is a radical of formula (a-1)

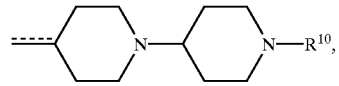

(a-2)

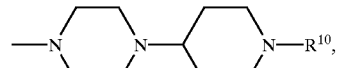

(a-3)

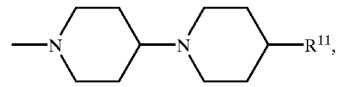

(a-4)

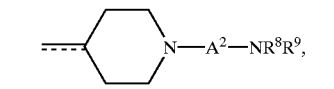

(a-5)

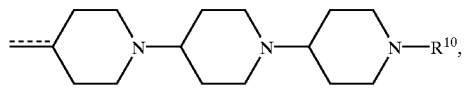

(a-6)

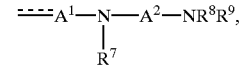

(a-7)

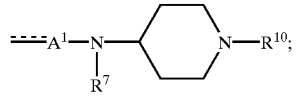

(a-8)

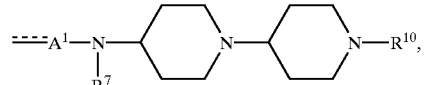

(a-9)

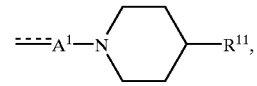

(a-10)

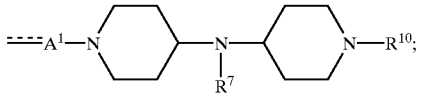

wherein $A^1$ is a direct bond or $C_{1-6}$alkanediyl; $A^2$ is $C_{2-6}$alkanediyl; and $R^7$ to $R^{11}$ are hydrogen, $C_{1-6}$alkyl, amino$C_{1-6}$alkyl and the like; having biocidal properties; their preparation, compositions containing them and their use as a biocide.

12 Claims, No Drawings

BIOCIDAL BENZYLBIPHENYL DERIVATIVES

CROSS REFERENCE TO RELATED APPLICATIONS

This application is the national stage of PCT/EP99/02098, filed Mar. 25, 1999, now WO 99/51578, which claims priority from EP Application No. 98201043.1, filed Apr. 2, 1998.

The present invention is concerned with novel compounds of formula (I) having biocidal properties. The invention further relates to methods for preparing such novel compounds, compositions comprising said novel compounds as well as the use as a biocide for material and plant protection applications.

Micro-organisms are extremely useful, and even indispensable, in processes such as, e.g. alcoholic fermentation, ripening of cheese, baking of bread, production of penicillin, purification of waste water, production of biogas, and the like. However, micro-organisms can also be harmful or highly dangerous; by causing infectious diseases, by forming poisonous or carcinogenic metabolites and by attacking valuable materials, disturbing production processes, or impairment of the quality of products.

Biocides are a broad and diverse group of compounds which are able to kill micro-organisms or inhibit the multiplication of micro-organisms. Biocides can be classified as bactericides, fungicides, algicides, insecticides, acaricides, molluscicides, herbicides and the like. Well-known biocides are, for example, formaldehyde releasing compounds, phenol derivatives, salicylanilides, carbanilides, and quaternary ammonium salts. An extensive overview of biocides is given in *"Microbiocides for the protection of materials"*, by Wilfried Paulus, Chapman & Hall, 1st edition, 1993.

An important group of the biocides are the bactericides. Since bacteria occur everywhere, their destructive activity (biodeterioration) is basically unavoidable. Nevertheless materials can be protected with the aid of compounds that prevent the multiplication of bacteria at the relevant sites, either by killing them or inhibiting their development.

The present invention provides for novel compounds of formula (I) unexpectedly having biocidal activity. In particular, said compounds of formula (I) have bactericidal activity.

Structurally related compounds have been described in EP-0,219,756-A1, published on Apr. 29, 1987, having fungicidal activity.

The compounds of the present invention differ from the prior art compounds by the nature of the L moiety.

The present invention concerns compounds of formula (1)

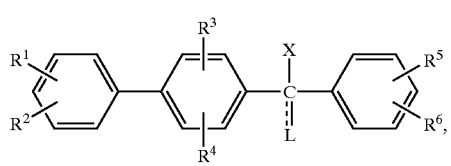

(I)

stereochemically isomeric forms thereof, acid or base addition salts thereof, N-oxides thereof, or quaternary ammonium derivatives thereof,
wherein
the dotted line is an optional bond;
X is a direct bond when the dotted line represents a bond, or
X is hydrogen or hydroxy, when the dotted line does not represent a bond;
$R_1$ and $R^2$ are each independently selected from hydrogen, halo, hydroxy, $C_{1-4}$alkyl, $C_{1-4}$alkyloxy, nitro, amino, cyano, trifluoromethyl, trifluoromethoxy, $C_{1-6}$alkylcarbonyl, hydroxycarbonyl, $C_{1-6}$alkyloxycarbonyl, aminocarbonyl, di($C_{1-4}$alkyl)aminocarbonyl, $C_{1-6}$alkylsulfinyl, $C_{1-6}$alkylsulfonyl, aminosulfonyl, di($C_{1-4}$alkyl)aminosulfonyl, or —SO$_3$H;
$R^3$ and $R^4$ are each independently selected from hydrogen, halo, hydroxy, $C_{1-4}$alkyl, $C_{1-4}$alkyloxy, nitro, amino, cyano, trifluoromethyl, or trifluoromethoxy;
$R^5$ and $R^6$ are each independently selected from hydrogen, halo, hydroxy, $C_{1-4}$alkyl, $C_{1-4}$alkyloxy, nitro, amino, cyano, trifluoromethyl, trifluoromethoxy, $C_{1-6}$alkylcarbonyl, hydroxycarbonyl, $C_{1-6}$alkyloxycarbonyl, aminocarbonyl, di($C_{1-4}$alkyl)aminocarbonyl, $C_{1-6}$alkylsulfinyl, $C_{1-6}$alkylsulfonyl, aminosulfonyl, di($C_{1-4}$alkyl)aminosulfonyl, or —SO$_3$H;
=L is a radical of formula

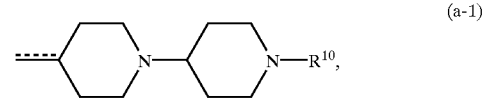
(a-1)

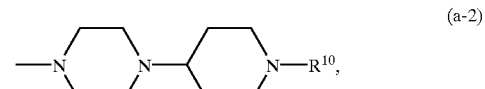
(a-2)

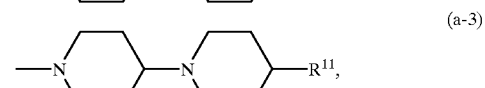
(a-3)

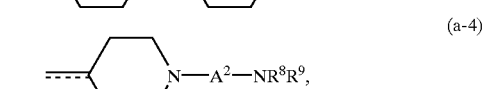
(a-4)

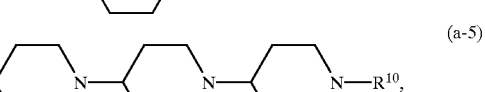
(a-5)

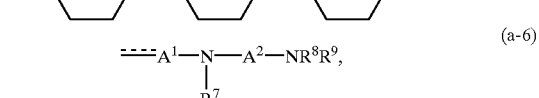
(a-6)

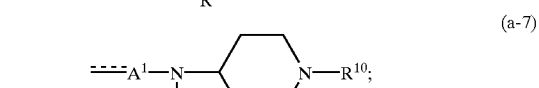
(a-7)

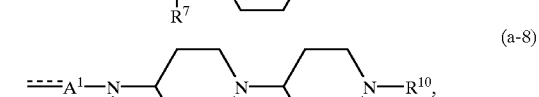
(a-8)

(a-9)

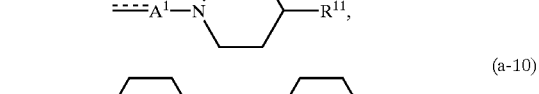
(a-10)

wherein
$A^1$ is a direct bond or $C_{1-6}$alkanediyl;

$A^2$ is $C_{2-6}$alkanediyl;

$R^7$ is hydrogen, $C_{1-4}$alkyl, phenyl or benzyl;

$R^8$ and $R^9$ are each independently hydrogen, $C_{1-6}$alkyl, amino$C_{1-6}$alkyl or mono- or di($C_{1-4}$alkyl)amino$C_{1-6}$alkyl;

$R^{10}$ is hydrogen, $C_{1-6}$alkyl, amino$C_{1-6}$alkyl or mono- or di($C_{1-4}$alkyl)amino$C_{1-6}$alkyl; and $R_{11}$ is hydrogen, $C_{1-6}$alkyl, amino, amino$C_{1-6}$alkyl or mono- or di($C_{1-4}$alkyl)amino$C_{1-6}$alkyl.

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; $C_{1-6}$alkyl is meant to include $C_{1-4}$alkyl and the higher homologues thereof having 5 or 6 carbon atoms, such as, for example, 2-methylbutyl, pentyl, hexyl and the like; $C_{1-6}$alkanediyl defines bivalent straight or branched chain hydrocarbon radicals containing from 1 to 6 carbon atoms such as, for example, methylene, 1,2-ethanediyl, 1,3-propanediyl, 1,4-butanediyl, 1,5-pentanediyl, 1,6-hexanediyl and the branched isomers thereof; $C_{2-6}$alkanediyl defines bivalent straight or branched chain hydrocarbon radicals containing from 2 to 6 carbon atoms such as, for example, 1,2-ethanediyl, 1,3-propanediyl, 1,4-butanediyl, 1,5-pentanediyl, 1,6-hexanediyl and the branched isomers thereof.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The invention also comprises the salts which the compounds of formula (1) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosphoric acid. Salt-forming sulfonic acids are toluenesulfonic acid, benzenesulfonic acid, methanesulfonic acid or trifluoromethane sulfonic acid. Salt-forming carboxylic acids are formic acid, acetic acid, propanoic acid, butanoic acid, and the like. Salt-forming dicarboxylic acids are oxalic acid, malonic acid, succinic acid, glutaric acid, and the like. Salt-forming hydroxy acids are glycolic acid, lactic acid, malic acid, tartaric acid, citric acid, mandelic acid, and the like. Other salt-forming carboxylic acids are trifluoroacetic acid, benzoic acid, chloroacetic acid, phthalic acid, maleic acid, and malonic acid. Phosphorus containing acids are the various phosphonous acids, phosphonic acids and phosphinic acids.

Particular addition salts are acid addition salts obtained by treating the base form of compounds of formula (I) with appropriate acidic biocidal agents such as, e.g. 1,2-benzisothiazolone (BIT), 5-chloro-1,2-benzisothiazolone, 6-chloro-1,2-benzisothiazolone, 5-fluoro-1,2-benzisothiazolone, 5-methyl-3(2H)-isothiazolone, or 4-bromo-5-methyl-3-isothiazolol. These addition salts can have different stoichiometry such as (1:1), (1:2), (1:3), (2:1), (3:1), (2:3) and so on.

Preferred salt-forming alkali metal hydroxides and earth alkaline metal hydroxides are the hydroxides of lithium, sodium, potassium, magnesium or calcium, most preferably those of sodium or potassium. Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine, diethanolamine and 1,4-diazabicyclo[2.2.2]octane being most preferred. Examples of quaternary ammonium bases are, in general, the cations of haloammonium salts, e.g. the tetramethylammonium cation, the trimethylbenzylammonium cation, the triethylbenzylammonium cation, and also the ammonium cation.

The term salt form also comprises metal complexes which the compounds of formula (I) may form. Metal complexes as mentioned above consist of a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like. Preferred are the metals pertaining to the transition elements of the fourth period. The metals may be present in each of their possible valences. The metal ions may be present in any of their possible valences, the most preferred metal copper being most advantageously used in its divalent form Cu(II). Suitable copper compounds are copper sulfate, acetate, hydroxide, oxide, borate, fluoride and in particular copper hydroxide carbonate $Cu(OH)_2CuCO_3$. The complexes can be mono- or polynuclear, they may contain one or more parts of the organic molecule as ligands.

The term addition salt as used hereinabove also comprises the solvates which the compounds of formula (I) as well as the salts thereof, are able to form. Such solvates are for example hydrates, alcoholates and the like.

A group of interesting compounds consists of those compounds of formula (I) wherein one or more of the following restrictions apply a) $R^1$ and $R^2$ are each independently selected from hydrogen, halo, or —SO$_3$H;

b) $R^3$ and $R^4$ are hydrogen;

c) $R^5$ and $R^6$ are each independently selected from hydrogen, halo, hydroxy, $C_{1-4}$alkyl, $C_{1-4}$alkyloxy or —SO$_3$H;

d) $R^7$ is hydrogen or $C_{1-4}$alkyl;

e) $R^8$ and $R^9$ are each independently hydrogen, $C_{1-4}$alkyl, or amino$C_{1-6}$alkyl;

f) $R^{10}$ is hydrogen, $C_{1-6}$alkyl, or di($C_{1-4}$alkyl)amino$C_{1-6}$alkyl;

g) $R^{11}$ is hydrogen, $C_{1-6}$alkyl, amino, amino$C_{1-6}$alkyl or di($C_{1-4}$alkyl)amino$C_{1-6}$alkyl;

h) $A^1$ is a direct bond or $C_{2-4}$alkanediyl;

g) $A^2$ is $C_{2-4}$alkanediyl.

More interesting compounds are those compounds of formula (I) wherein L is a radical of formula (a-1), (a-2), (a-3), (a-5), (a-7), (a-8), or (a-10), wherein $R^{10}$ is hydrogen, $C_{1-6}$alkyl, or di($C_{1-4}$alkyl)amino$C_{1-6}$alkyl.

Other more interesting compounds are those compounds of formula (I) wherein L is a radical of formula (a-3) or (a-9) wherein $R^{11}$ is hydrogen, $C_{1-6}$alkyl, amino, (amino$C_{1-6}$alkyl or di($C_{1-4}$alkyl)amino$C_{1-6}$alkyl.

Also more interesting compounds are those compounds of formula (I) wherein L is a radical of formula (a-4) or (a-6) wherein $R^8$ and $R^9$ are each independently hydrogen, $C_{1-4}$alkyl, or amino$C_{1-6}$alkyl.

Particular compounds are those compounds of formula (I) wherein L is a radical of formula (a-1) wherein $R^{10}$ is hydrogen.

Other particular compounds are those compounds of formula (I) wherein L is a radical of formula (a-4) wherein $A^2$ is $C_{2-4}$alkanediyl and $R^8$ and $R^9$ are each independently hydrogen or $C_{1-4}$alkyl.

Further particular compounds are those compounds of formula (I) wherein L is a radical of formula (a-6) wherein $A^1$ and $A^2$ are $C_{2-4}$alkanediyl, $R^7$ is hydrogen or $C_{1-4}$alkyl, and $R^8$ and $R^9$ are each independently hydrogen or $C_{1-4}$alkyl.

Preferred compounds are
4-[[(1,1'-biphenyl)-4-yl]phenylmethyl](1,4'-bipiperidine);
4-[[(1,1'-biphenyl)-4-yl]phenylmethyl]-1-piperidinepropanamine; and
N-[3-[(1,1'-biphenyl)-4-yl]-3-phenylpropyl]-1,3-propanediamine;
and acid or base addition salts, the stereoisomeric forms, the N-oxides, or quaternary ammonium derivatives thereof.

Other preferred compounds are the acid addition salts obtained by treating the base form of compounds of formula (I) with appropriate acidic biocidal agents such as, e.g. 1,2-benzisothiazolone (BIT).

Particular preferred acid addition salts are the BIT salts of
4-[[(1,1'-biphenyl)-4-yl]phenylmethyl](1,4'-bipiperidine),
4-[[(1,1'-biphenyl)-4-yl]phenylmethyl]-1-piperidinepropanamine, and
N-[3-[(1,1'-biphenyl)-4-yl]-3-phenylpropyl]-1,3-propanediamine;
or the BIT salts of a stereoisomeric form, an N-oxide, or a quaternary ammonium derivative of the latter compounds.

Compounds of formula (I-a), defined as compounds of formula (I) wherein X is hydroxy and the dotted line does not represent a bond, can be prepared by reacting an organometallic derivative of an intermediate of formula (II), wherein halo represents chloro, bromo or iodo, with an intermediate of formula (III). Said organometallic derivative of an intermediate of formula (II) can be prepared, for instance, by converting said intermediate (II) into its corresponding Grignard analogue using magnesium in a reaction-inert solvent such as, e.g. diethyl ether or tetrahydrofuran. For those compounds of formula (I-a) wherein the radical L bears a radical of formula $R^8$, $R^9$ or $R^{10}$ being hydrogen, depending upon the reaction conditions it can be advisable to temporarily protect said $R^8$, $R^9$ or $R^{10}$ by converting $R^8$, $R^9$ or $R^{10}$ into an appropriate protecting group such as, e.g. $C_{1-6}$alkyloxycarbonyl.

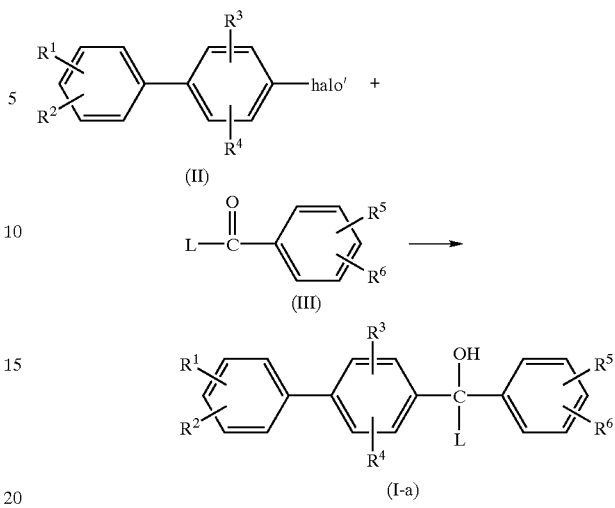

Compounds of formula (I-a) can be converted to compounds of formula (I-b), being compounds of formula (I) wherein X is a direct bond and the dotted line represents a bond, by dehydrating said compounds of formula (I-a) under art-known reaction conditions as exemplified, for instance, in example B.3.

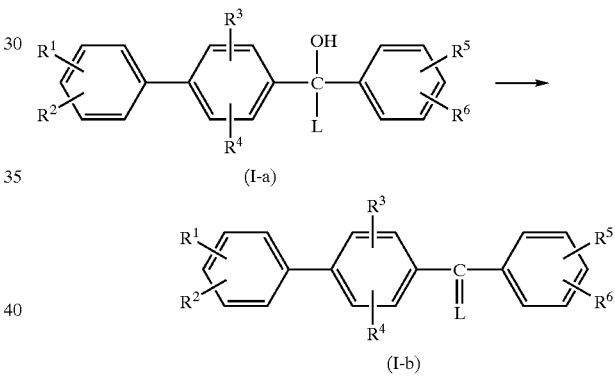

Compounds of formula (I-b) can be converted to compounds of formula (I-c), being compounds of formula (I) wherein X is hydrogen and the dotted line does not represent a bond, by hydrogenating said compounds of formula (I-a).

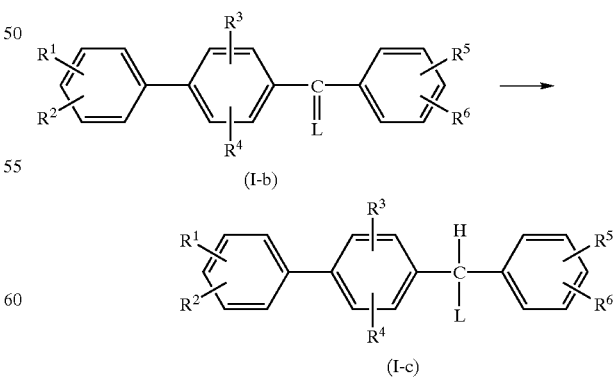

Compounds of formula (I-c-1), defined as compounds of formula (I-c) wherein $L^1$ represents a radical of formula (a-2), (a-3), (a-6) to (a-10) wherein $A^1$ is a direct bond, can be prepared by alkylating an intermediate of formula (V) with an intermediate of formula (IV), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile, and optionally in the presence of a suitable base such as, for example, sodium carbonate, potassium carbonate or triethylamine. For those compounds of formula (I-c-1) wherein the radical $L^1$ bears a radical of formula $R^8$, $R^9$ or $R^{10}$ being hydrogen, depending upon the reaction conditions it can be advisable to temporarily protect said $R^8$, $R^9$ or $R^{10}$ by converting $R^8$, $R^9$ or $R^{10}$ into a suitable protecting group such as, e.g. $C_{1-6}$alkyloxycarbonyl.

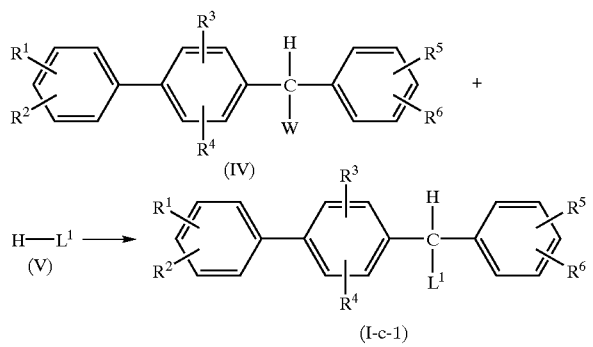

Compounds of formula (I-d), defined as compounds of formula (I) wherein $L^2$ represents a radical of formula (a-6) to (a-10) wherein $A^1$ is $C_{1-6}$alkanediyl, can be prepared by N-alkylating an intermediate of formula (VII) with an intermediate of formula (VI), wherein W is a leaving group as defined herein-above.

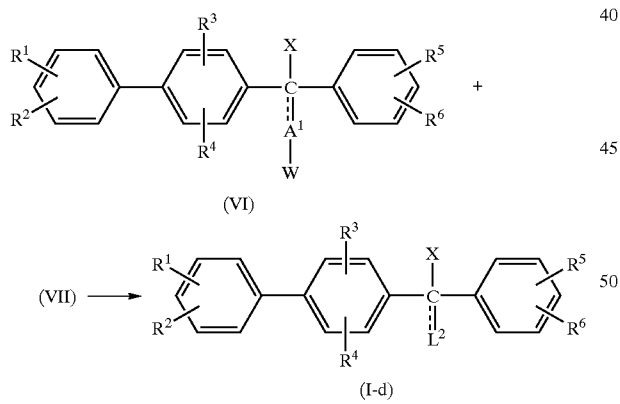

Said intermediate of formula (VII) has one of the following structures:

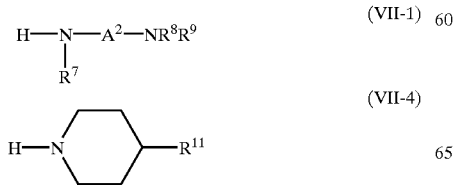

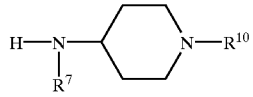

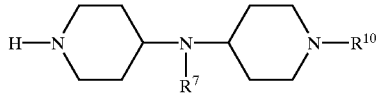

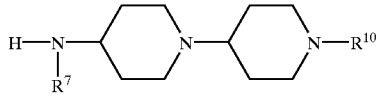

For those intermediates of formula (VII) wherein the radical of formula $R^7$, $R^8$, $R^9$ or $R^{10}$ is hydrogen, depending upon the reaction conditions, it can be advisable to temporarily protect said $R^7$, $R^8$, $R^9$ or $R^{10}$ by converting $R^7$, $R^8$, $R^9$ or $R^{10}$ into a suitable protecting group such as, e.g. $C_{1-6}$alkyloxycarbonyl.

Compounds of formula (I-e), defined as compounds of formula (I) wherein $L^3$ represents a radical of formula (a-2) or (a-4) can be prepared by reductively N-alkylating an intermediate of formula (VIII) with an intermediate of formula (IX-1) or (X-1); or by N-alkylating said intermediate of formula (VIII) with an intermediate of formula (IX-2) or (X-2).

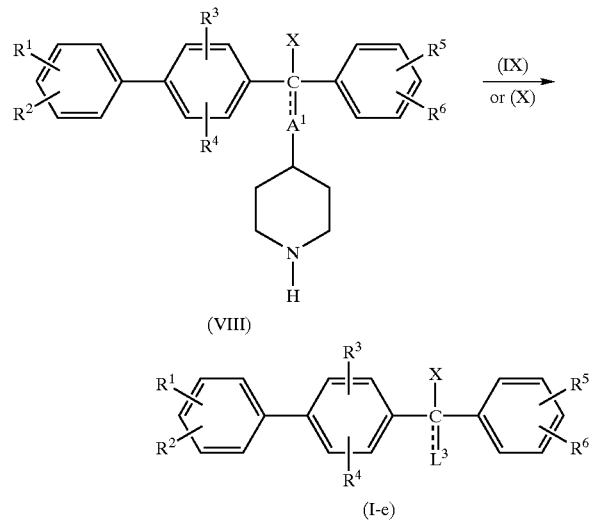

Said intermediate of formula (IX) or (X) has the following structure:

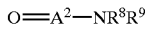

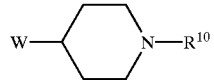

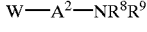

For those intermediates of formula (IX) or (X) wherein the radical of formula $R^8$, $R^9$ or $R^{10}$ is hydrogen, depending upon the reaction conditions, it can be advisable to temporarily protect said $R^8$, $R^9$ or $R^{10}$ by converting $R^8$, $R^9$ or $R^{10}$ into a suitable protecting group such as, e.g. $C_{1-6}$alkyloxycarbonyl.

The compounds of formula (I) may also be converted into each other via art-known reactions or functional group transformations. For instance, compounds of formula (I) wherein $R^{10}$ or $R^{11}$ are hydrogen can be converted into compounds of formula (I) wherein $R^{10}$ or $R^{11}$ is $C_{1-6}$alkyl using art-known N-alkylation procedures.

Intermediates of formula (IV) can be prepared as described in working example A.7, intermediates of formula (VI) can be prepared as described in working examples A.5 and A.6, and intermediates of formula (VIII) can be prepared as described in working examples A.2 and A.3.

The starting materials and some of the intermediates are known compounds and are commercially available or may be prepared according to conventional reaction procedures generally known in the art.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The biocidal properties of the compounds of formula (I) are exemplified in the biological section C herein-below, In particular, the compounds of formula (I) have bactericidal properties as evidenced in examples C. 1 and C.2.

Furthermore, the compounds of formula (I) were also found to be active against certain yeasts, as evidenced in example C.3.

A number of compounds of formula (I) also have algicidal properties.

The compounds of the present invention are active against a broad range of bacteria, both gram-positive as gram-negative bacteria. As examples of such gram-positive bacteria there may be named *Micrococcus flavus, Staphylococcus aureus, Staphylococcus epidermidis, Streptococcus faecalis,* and the like. As example of such gram-negative bacteria there may be named *Pseudomonas aeruginosa, Pseudomonas putida, Pseudomonas stutzeri, Pseudomonas cepacia, Pseudomonas fluorescens,* Pseudomonas sp., *Proteus vulgaris, Proteus morganii, Eschericia coli, Klebsiella aerogenes, Enterobacter cloacae, Salmonella typhimurium, Serratia marcescens,* and the like. Experience has shown that gram-negative bacteria (which are additionally protected by an outer membrane compared to gram-positive bacteria), especially Pseudomonades, are more resistant than gram-positive bacteria against biocides (*"Microbiocides for the protection of materials"*, by Wilfried Paulus, Chapman & Hall, 1st edition, 1993). Therefore, compounds having bactericidal properties against gram-negative bacteria, especially against Pseudomonades, are highly desirous.

The compounds of formula (I) can be used in a variety of applications industrial aqueous process fluids, e.g. cooling waters, pulp and papermill process waters and suspensions, secondary oil recovery systems, spinning fluids, metal working fluids, and the like in-tank/in-can protection of aqueous functional fluids, e.g. polymer emulsions, water based paints and adhesives, glues, starch slurries, thickener solutions, gelatine, wax emulsions, inks, polishes, pigment and mineral slurries, rubber latexes, concrete additives, drilling muds, toiletries, aqueous cosmetic formulations, pharmaceutical formulations, and the like antimicrobial treatment of materails that finally contain little or no water in a free state, e.g. paints and adhesive films, textiles, paper, paperboards, plastics, hoses, cords, rubber product, leather, wood, timber materials, and the like disinfection of inanimate surfaces (e.g. in hospitals, households, animal stables, the food industry) and equipment.

The compounds of formula (I) can be used for the protection of plants and plant-derived materials from degradation by phytopathogenic bacteria. As examples of such phytopathogenic bacteria there may be named *Xanthomonas campestris* pv. *phaseoli, Pseudomonas syringae* pv. *phaseolicola, Erwinia amylovora, Agrobacterium tumefaciens, Clavibacter michiganense, Erwinia carotovora, Erwinia tracheiphila, Pseudomonas pisi, Pseudomonas solanacearum, Streptomyces scabies, Xylella fastidiosa,* and the like. Hence, the compounds of formula (I) possess advantageous curative, preventive and systemic biocidal activity to protect plants, in particular culture plants. Said compounds of formula (I) can be used to protect plants or parts of plants, e.g. fruits, blossoms, flowers, foliage, stems, roots, tubers of plants or culture plants infected, harmed or destroyed by micro-organisms, whereby later-growing parts of plants are protected against such micro-organisms.

The compounds of formula (I) can further be used in seed disinfection (fruits, tubers, cereal grains) and to treat plant cuttings as well as to combat phytopathogenous microorganims occurring in the soil.

As examples of the wide variety of culture plants in which the compounds of the present invention can be used, there may be named for example cereals, e.g. wheat, barley, rye, oats, rice, sorghum and the like; beets, e.g. sugar beet and fodder beet; pome and stone fruits and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruits, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugar-cane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not to delimiting it thereto.

The compounds of formula (I) and compositions comprising one or more of these compounds can also be used to prevent the formation of biofilms. Biofilms are composed of millions of microorganisms (bacteria, fungi, algae, and protozoa) that accumulate on surfaces in aqueous environments (*Science,* vol. 273, p. 1795–1797, 1996). These film-forming microbes excrete a glue-like substance that anchors them to materials such as metals, plastics, tissue, and soil particles. Once anchored to a surface, biofilm microorganisms carry out a variety of detrimental or beneficial reactions, depending on the surrounding conditions. Some of the problems associated with biofilm formation include biofouling (fouling or contamination linked to microbial activity), biocorrosion (especially of industrial pipes), oil field souring (the reduction of sulfates by microbes in soil) and infections caused by biofilm growing on host tissues or medical implants. Biofilm-related problems cost industry billions of dollars annually by corroding pipes, reducing heat transfer or hydraulic pressure in industrial cooling systems, plugging water injection jets, and clogging water filters. In addition, biofilms cause major medical problems through infecting host tissues, harboring bacteria that contaminate drinking water, causing rejection of medical implants, and contamination of medical devices ranging from contact lenses, urinary catheters to artificial hearts.

The compounds of formula (I) are stable compounds and no precautionary measures are required for handling them.

In view of the biological activity of the compounds of formula (I) as demonstrated in examples C.1 to C.4, the subject compounds are useful for controlling, i.e. preventing, inhibiting, eliminating, combatting, or eradicating, micro-organisms.

The invention also relates to biocidal compositions containing one or more inert carriers and, if desired, other adjuvants and as active ingredient a biocidally effective amount of a compound of formula (I) as defined hereinabove. Further the invention relates to a method of controlling micro-organisms, in particular bacteria, by the application of the novel compounds to said micro-organisms.

In the method for controling micro-organisms according to the invention the compounds of formula (I) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. Depending on the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, such as, alkylbenzene mixtures, e.g. dimethylbenzene mixtures or alkylated naphthalenes, aliphatic or alicyclic hydrocarbons such as paraffins, cyclohexane or tetrahydronaphtalene, alcohols such as ethanol, propanol or butanol, glycols and their ethers and esters, such as propylene glycol or dipropylene glycol ether, ketones such as cyclohexanone, isophorone or diacetone alcohol, strongly polar solvents such as N-methyl-2-pyrrolidone, dimethylsulfoxide or water, vegetable oils and their esters, such as rape, castor or soybean oil, possibly also silicon oil.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, earth alkaline metal salts or unsubstitued or substituted ammonium salts and contain a $C_{8-22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

Compositions comprising a compound of formula (I) may further comprise other active ingredients, e.g. other biocides, in particular fungicides, bactericides, acaricides, nematicides, insecticides or herbicides, for example so as to widen the spectrum of action or to prevent the build up of resistance. In many cases, this results in synergistic effects, i.e. the activity of the mixture exceeds the activity of the individual components.

As biocidal agents, which may be used in combination with the compounds of the present invention there may be considered products of the following classes:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N -methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram. Particular fungicides are thiabendazole; isothia- and benzisothiazolone derivatives such as, e.g. 1,2-benzisothiazolone (BIT); oxathiazines such as bethoxazin (i.e. 3-(benzo[b]thien-2-yl)-5,6-dihydro-1,4,2-oxathiazine, 4-oxide); and fungicidally active triazoles such as, for example, azaconazole, bromuconazole, cyproconazole, difenoconazole, epoxiconazole, fenbuconazole, hexaconazole, metconazole, penconazole, propiconazole, tebuconazole, or triticonazole.

Bactericides bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicide abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos chlorfenvinphos, chlorfluazuron, chliormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

Other biocidal agents that may be used in combination with the compounds of the present invention there may be considered products of the following classes: phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol, chlorinated hydrodiphenylethers such as, for example, 2-hydroxy-3,2'4'-trichloro-diphenylether, phenylphenol, 4-chloro-2-phenylphenol, 4-chloro-2-benzylphenol, dichlorophene, hexachlorophene; aldehydes such as formaldehyde, glutaraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; mono-, di- and polyamines such as dodecylamine or 1,10-di(n-heptyl)-1,10-diaminodecane; sulfonium- and phosphonium compounds; mercapto compounds as well as their alkali, earth alkaline and heavy metal salts such as 2-mercaptopyridine-N-oxide and its sodium and zinc salt, 3-mercaptopyridazin-2-oxide, 2-mercaptoquinoxaline-1-oxide, 2-mercaptoquinoxaline-di-N-oxide, as well as the symmetrical disulfides of said mercapto compounds; ureas such as tribromo- or trichlorocarbanilide, dichlorotrifluoromethyl-diphenylurea; tribromosalicylanilide; 2-bromo-2-nitro-1,3-dihydroxypropane; dichlorobenzoxazolon; and chlorohexidine.

The biocidal compositions which are preferably employed in the method of the invention usually contain 0.1 to 99%, preferably 0.1 to 95% of a compound of formula (I), 1 to 99% of a solid or liquid adjuvant, and 0 to 25% preferably 0.1 to 25% of a surfactant. The commercial forms of said biocidal compositions are advantageously concentrates which can easily be diluted by the end user.

The compositions can also contain further additives, such as, stabilizers, e.g. optionally epoxidized vegetable oils (epoxidized coconut, rape or soybean oil), defoamers, e.g. silicon oil, conservatives, viscosity regulators, binding materials, fillers and dung or other materials for special purposes.

The present invention also relates to compositions comprising a compound of formula (I) and another active ingredient, as enumerated hereabove, in quantities producing a synergistic effect, and a carrier. In particular, synergistic compositions of a compound of formula (I) with another bacteride and/or another fungicide are envisaged.

Preferred formulations are composed in particular of the following constituents (%=percentage by weight):

Emulsifiable Concentrates
  active ingredient: 1 to 9%, preferably 2 to 5%
  surfactant: 5 to 30% preferably 10 to 20%
  liquid carrier: 5 to 94% preferably 70 to 85%
Dusts
  active ingredient: 0.1 to 10%, preferably 0.1 to 1%
  solid carrier: 99.9 to 90%, preferably 99.9 to 99%

Suspension Concentrates
  active ingredient: 5 to 75%, preferably 10 to 50%
  water: 94 to 24%, preferably 88 to 30%
  surfactant: 1 to 40%, preferably 2 to 30%
Wettable Powders
  active ingredient: 0.5 to 90%, preferably 1 to 80%
  surfactant: 0.5 to 20%, preferably 1 to 15%
  solid carrier: 5 to 95%, preferably 15 to 90%
Granulates
  active ingredient: 0.5 to 30%, preferably 3 to 15%
  solid carrier: 99.5 to 70%, preferably 97 to 85%

The following examples are intended to illustrate the present invention.

Experimental Part

In the procedures described hereinafter the following abbreviations were used: "ACN" stands for acetonitrile; "THF", which stands for tetrahydrofuran; "DCM" stands for dichloromethane; "DIPE" stands for diisopropylether; "EtOAc" stands for ethyl acetate; "NH$_4$OAc" stands for ammonium acetate; "HOAc" stands for acetic acid; "MIK" stands for methyl isobutyl ketone.

For some chemicals the chemical formula was used, e.g. NaOH for sodium hydroxide, $K_2CO_3$ for potassium carbonate, $H_2$ for hydrogen gas, $MgSO_4$ for magnesium sulfate, $CuO.Cr_2O_3$ for copper chromite, $N_2$ for nitrogen gas, $CH_2Cl_2$ for dichloromethane, $CH_3OH$ for methanol, $NH_3$ for ammonia, HCl for hydrochloric acid, NaH for sodium hydride, $CaCO_3$ for calcium carbonate, CO for carbon monoxide, and KOH for potassium hydroxide.

Of some compounds of formula (I) the absolute sterochemical configuration was not experimentally determined. In those cases the stereochemically isomeric form which was first isolated is designated as "A" and the second as "B", without further reference to the actual stereochemical configuration.

Preparation of the Intermediates

EXAMPLE A.1 a) A mixture of (4-fluorophenyl) (4-piperidinyl) methanone hydrochloride (1:1) (0.38 mol) and 4-oxo-1-piperidinecarboxylic acid, ethyl ester (0.38 mol) in methanol (700 ml) was hydrogenated at 50° C. with palladium on activated carbon (5 g) as a catalyst in the presence of potassium acetate (50 g) and thiophene solution (5 ml). After uptake of hydrogen (2 equivalents), the catalyst was filtered off and the filtrate was evaporated. The residue was dissolved in DCM, washed with $H_2O$, dried, filtered and the solvent was evaporated. The residue was triturated in 2-propanol, filtered off and dried, yielding 78 g of (4-fluorophenyl) (4-piperidinyl)methanone hydrochloride (interm. 1).

b) A solution of 4-bromo-1,1'-biphenyl (0.1 mol) in THF (200 ml) was added dropwise to a mixture of magnesium (0.1 mol) in THF (50 ml). The Grignard complex was formed. The mixture was stirred and refluxed for 30 minutes. A solution of intermediate (1) (0.05 mol) in THF (50 ml) was added dropwise. The mixture was stirred and refluxed for 6 hours, then cooled, poured out into a NH4Cl solution and extracted with toluene. The organic layer was separated, washed with $H_2O$, dried, filtered and the solvent was evaporated. The residue was purified by column chromatography over silica gel (eluent: $CH_2Cl_2/CH_3OH$ 99/1). The pure fractions were collected and the solvent was evaporated, yielding 31 g of (±)-ethyl 4-[[(1,1'-biphenyl)-4-yl](4- fluorophenyl)hydroxymethyl](1,4'-bipiperidine)-1'-carboxylate (interm. 2)

EXAMPLE A.2 a) 12.5 g of acetyl-4-piperidinecarbonyl chloride were added portionwise to a mixture of 10 g of 4-fluoro-1,1'-biphenyl, 17.5 g of aluminum-(III)-chloride and 60 g of 1,2-di-chloroethane. Upon completion, stirring was continued for 1 hour at reflux temperature. The reaction mixture was poured into a mixture of crushed ice and hydrochloric acid. The product was extracted with DCM. The extract was dried, filtered and evaporated. The residue was crystallized from 2-propanol. The product was filtered off and dried, yielding 15 g (80.8%) of 1-acetyl-4-[(4'-fluoro-[1,1'-biphenyl]-4-yl)carbonyl]piperidine (interm. 3).

b) A mixture of 15 g of intermediate (3) and a HCl solution (6 N, 100 ml) was stirred for 3 hours at reflux temperature. After cooling, the precipitated product was filtered off and suspended in water. The base was liberated in the conventional manner with sodium hydroxide and extracted with dichloromethane. The extract was dried, filtered and evaporated, yielding 11 g (84.3%) of (4'-fluoro-[1,1'-biphenyl]-4-yl) (4-piperidinyl)-methanone (interm. 4).

c) To a stirred mixture of 11 g of intermediate (4), 4.5 g of N,N-diethylethanamine and 150 g of trichloromethane were added dropwise 5 g of ethyl carbonochloridate. Upon complete addition, stirring was continued for 1 hour at reflux temperature. After cooling, the reaction mixture was washed with water, dried, filtered and evaporated, yielding 13 g (91.4%) of 4-[(4'-fluoro-[1,1'-biphenyl]-4-yl)carbonyl]-1-piperidinecarboxylate (interm. 5).

d) A solution of bromobenzene (0.118 mol) in THF (50 ml) was added dropwise to a mixture of magnesium (0.118 mol) in THF (10 ml). The mixture was stirred and refluxed for 30 minutes and then cooled. A solution of intermediate (5) (0.059 mol) in THF (140 ml) was added dropwise. The mixture was stirred and refluxed overnight, then cooled, poured out into a saturated $NH_4Cl$ solution and extracted with toluene. The organic layer was separated, washed with $H_2O$, dried, filtered and the solvent was evaporated. The residue was purified over silica gel on a glass filter (eluent: $CH_2C_2$ 100%). The pure fractions were collected and the solvent was evaporated, yielding 27 g (100%) of (±)-ethyl 4-[[4'-fluoro(1,1'-biphenyl)-4-yl]hydroxyphenylmethyl]-1-piperidinecarboxylate (interm. 6)

e) A mixture of intermediate (6) (0.062 mol) in HBr (48%, 250 ml) was stirred and refluxed for 4 hours. The solvent was evaporated. The residue was dissolved in DCM, alkalized with $NH_4OH$ and extracted with DCM. The organic layer was separated, washed with $H_2O$, dried, filtered and the solvent was evaporated, yielding 19 g (89%) of 4-[[4-fluoro(1,1'-biphenyl)-4-yl]phenylmethylene]piperidine (interm.7).

f) A mixture of intermediate (7) (0.055 mol) and 4-oxo-1-piperidinecarboxylic acid, ethyl ester (0.055 mol) in methanol (250 ml) was hydrogenated at 50° C. with palladium on activated carbon (2 g) as a catalyst in the presence of thiophene solution (1 ml). After uptake of hydrogen (1 equivalent), the catalyst was filtered off and the filtrate was evaporated, yielding 25.5 g (90%) of ethyl 4-[[4'-fluoro(1,1'-biphenyl)4-yl]phenylmethylene](1,4'-bipiperidine)-1'-carboxylate (interm. 8).

EXAMPLE A.3 a) A mixture of 1,1'-biphenyl (0.3 mol) and aluminum-(III)-chloride (0.6 mol) in 1,2-dichloroethane (500 ml) was stirred. A mixture of ethyl 4-(chlorocarbonyl)-1-piperidinecarboxylate (0.3 mol) in 1,2-dichloroethane (100 ml) was added dropwise over a 30-minutes period (exothermic temperature rise to 30° C.). The mixture was stirred at room temperature for 90 minutes, poured out into ice and HCl and extracted with DCM. $CH_3OH$ was added. The organic layer was separated, dried, filtered and the solvent was evaporated. The residue was purified by column chromatography over silica gel (eluent: $CH_2Cl_2/CH_3OH$ 99/1). The pure fractions were collected and the solvent was evaporated. The residue was crystallized from DIPE. The precipitate was filtered off and dried, yielding 42 g of ethyl 4-(4-phenylbenzoyl)-1-piperidinecarboxylate (interm. 9).

b) A mixture of 1-bromo-4-methoxybenzene (0.053 mol) in THF (150 ml) was added dropwise under nitrogen flow to a stirring mixture of magnesium (0.053 mol) and a few crystals of $I_2$ in THF (50 ml). The mixture was stirred and refluxed for 1 hour. A mixture of intermediate (9) (0.044 mol) in THF (300 ml) was added dropwise. The mixture was stirred and refluxed for 1 hour, poured out into a saturated $NH_4Cl$ solution (300 ml) and extracted three times with DCM. The combined organic layer was washed once with H2O and once with a saturated NaCl solution, dried, filtered and the solvent was evaporated. This fraction was crystallized from $CH_3OH$/DIPE. The precipitate was filtered off and dried, yielding 13.2 g (67%) of (±)-ethyl 4-[[(1,1'-biphenyl)-4-yl](4-methoxyphenyl)hydroxymethyl]-1-piperidinecarboxylate (interm.10).

c) A mixture of intermediate (10) (0.029 mol) in methanol (250 ml) was hydrogenated at 50° C. with palladium on activated carbon (2 g) as a catalyst. After uptake of hydrogen (1 equivalent), the catalyst was filtered off and the filtrate was evaporated, yielding 12.5 g (100%) of (±)-ethyl 4-[[(1,1'-biphenyl)-4-yl](4-methoxyphenyl)-methyl]-1-piperidinecarboxylate (interm. 11).

d) A mixture of intermediate (11) (0.029 mol) and potassium hydroxide (20 g) in 2-propanol (200 ml) was stirred and refluxed for 4 hours and then cooled. The solvent was evaporated. The residue was dissolved in $H_2O$ (250 ml) and the mixture was extracted three times with DCM. The combined organic layer was washed twice with $H_2O$ and once with a saturated NaCl solution, dried, filtered and the solvent was evaporated. The residue was purified by column chromatography over silica gel (eluent 1: $CH_2Cl_2/CH_3OH$ 100/0 to 95/5, eluent 2: $CH_2Cl_2$ /($CH_3OH/NH_3$)90/10). The desired fractions were collected and the solvent was evaporated, yielding 8.2 g (79%) of (±)-4-[[(1,1'-biphenyl)-4-yl](4-methoxyphenyl)methyl]piperidine (interm. 12).

EXAMPLE A.4 a) A mixture of bromobenzene (0.2 mol) in diethyl ether (200 ml) was added dropwise to a mixture of magnesium (0.2 mol) in diethyl ether (20 ml). The mixture was stirred and refluxed for 1 hour. A mixture of intermediate (9) (0.1 mol) in diethyl ether (800 ml) was added dropwise. The mixture was stirred and refluxed for 1 hour, cooled, poured out into a $NH_4Cl$ solution and extracted with toluene. The organic layer was separated, washed, dried, filtered and the solvent was evaporated. The residue was triturated in DIPE, filtered off and dried, yielding 30 g of (±)-ethyl 4-[[(1,1'-biphenyl)4-yl]hydroxyphenylmethyl]-1-piperidinecarboxylate (interm. 13).

b) A mixture of intermediate (13) (0.0722 mol) in a mixture of 2-propanol and HCl (50 ml) and toluene (500 ml) was stirred and refluxed for 4 hours using a water separator. The solvent was evaporated. The residue was dissolved in DCM. The organic solution was washed, dried, filtered and the solvent was evaporated, yielding 31 g of ethyl 4-[[(1,1'-biphenyl)-4-yl]phenylmethylene]-1-piperidinecarboxylate (interm. 14).

c) A mixture of intermediate (14) (0.078 mol) in methanol (250 ml) was hydrogenated at 50° C. for 2 days with palladium on activated carbon (2 g) as a catalyst. After uptake of hydrogen (1 equivalent), the catalyst was filtered off and the filtrate was evaporated, yielding 27 g of (±)-ethyl 4-[[(1,1'-biphenyl)-4-yl]phenylmethyl]-1-piperidinecarboxylate (interm. 15).

d) A mixture of intermediate (15) (0.023 mol) and sodium hydrogen sulfite (1 g) in hydrobromic acid (48%) (250 ml) was stirred and refluxed for 6 hours, then cooled and allowed to crystallize out. The precipitate was filtered off and dried, yielding 5.29 g (69%) of product. This fraction was separated into its enantiomers by HPLC (eluent: hexane/ethanol 40/60; column: CHIRALPAK AD 5 cm). Two pure fractions were collected and their solvents were evaporated, yielding 2.4 g of fraction 1 and 2.2 g of fraction 2.

Fraction 1 was taken up in a HBr solution (0.5ml). The solvent was evaporated. Toluene was added twice and evaporated again. The residue was crystallized from 2-propanol. The precipitate was filtered off and dried, yielding (−)-4-[[(1,1'-biphenyl)-4-yl]phenylmethyl]piperidine; $[\alpha]_D^{20}=-7.62°$ (c=0.5% in $CH_3OH$) (interm. 16). Fraction 2 was taken up in a HBr solution (0.5 ml). The solvent was evaporated. Toluene was added twice and evaporated again. The residue was crystallized from 2-propanol. The precipitate was filtered off and dried, yielding (+)-4-[[(1,1'-biphenyl)-4-yl]phenylmethyl]piperidine; $[\alpha]_D^{20}=+6.22°$ (c=0.5% in $CH_3OH$) (interm. 26).

e) A mixture of intermediate (16) (0.0046 mol) and 4-oxo-1-piperidinecarboxylic acid, 1,1-dimethylethyl ester (0.0048 mol) in methanol (150 ml) was hydrogenated at room temperature with palladium on activated carbon (10%) (1 g) as a catalyst in the presence of potassium acetate (2 g) and a solution of thiophene in methanol (4%) (1 ml). After uptake of hydrogen (1 equivalent), the catalyst was filtered off and the filtrate was evaporated. The residue was converted into the free base and purified by column chromatography over silica gel (eluent: $CH_2Cl_2/CH_3OH$ 100/0 to 98/2). The pure fractions were collected and the solvent was evaporated, yielding 1 g of 1,1-dimethylethyl (A)-4-[[(1,1'-biphenyl)-4-yl]phenylmethyl](1,4'-bipiperidine)-1'-carboxylate (interm. 17).

EXAMPLE A.5 a) A dispersion of sodium hydride in a mineral oil (60%) (0.22 mol) was treated with hexane under $N_2$ flow to remove the oil and then dispensed in THF (100 ml) under $N_2$ flow. Ethyl (diethylphosphono)acetate (0.22 mol) was added dropwise. The mixture was stirred for 30 minutes until the gas development has stopped. A mixture of (1,1'-biphenyl)-4-ylphenylmethanone (0.2 mol) in THF (100 ml) was added dropwise at room temperature. The mixture was stirred at room temperature for 1 hour, then stirred and refluxed for 17 hours, cooled, poured out into HCl 10% and ice and extracted three times with DCM. The combined organic layer was washed once with a saturated $K_2CO_3$ solution, twice with $H_2O$ and once with a saturated NaCl solution, then dried, filtered and the solvent was evaporated. The residue was purified by column chromatography over silica gel (eluent: $CH_2Cl_2$/EtOAc/hexane 1/1/98). Two pure fractions were collected and their solvents were evaporated. Fraction 2 was crystallized from 2-propanol. The precipitate was filtered off and dried. The mother layer was evaporated and combined with fraction 1, yielding 45 g of ethyl 3-[(1,1'-biphenyl)4-yl]-3-phenyl-2-propenoate (interm. 18).

b) A mixture of intermediate (18) (0.137 mol) in methanol (500 ml) was hydrogenated at room temperature under a 1 atm pressure with palladium on activated carbon (10%) (4 g) as a catalyst in the presence of a solution of thiophene in DIPE (1 ml). After uptake of hydrogen (1 equivalent), the catalyst was filtered off and the filtrate was evaporated. This fraction was crystallized from $CH_3OH$. The precipitate was filtered off and dried, yielding 28 g (62%) of (±)-ethyl 3-[(1,1'-biphenyl)4-yl]-3-phenyl-propanoate (interm. 19).

c) Lithium aluminum hydride (0.057 mol) in THF (200 ml) was stirred at reflux temperature. A solution of intermediate (19) (0.057 mol) in THF (300 ml) was added dropwise and the resulting reaction mixture was stirred and refluxed for 3 hours, then stirred overnight at room temperature. The mixture was decomposed with water (5 ml), then acidified with 4N $H_2SO_4$. The reaction mixture was filtered and the filtrate was evaporated. The residue was purified over silica gel on a glass filter (eluent: $CH_2Cl_2$). The desired fractions were collected and the solvent was evaporated, yielding 14 g of (±)-γ-phenyl(1,1'-biphenyl)-4-propanol (interm. 20).

d) A mixture of intermediate (20) (0.048 mol) in DCM (150 ml) and pyridine (150 ml) was stirred at room temperature. Methanesulfonyl chloride (0.06 mol) was added dropwise and the resulting reaction mixture was stirred for 3 hours at room temperature. The solvent was evaporated. The residue was dissolved in DCM. The organic solution was washed with water, dried, filtered and the solvent was evaporated. The residue was purified by column chromatography over silica gel (eluent: $CH_2Cl_2$). The desired fractions were collected and the solvent was evaporated. The residue was triturated under DIPE, filtered off and dried, yielding 5.5 g of (±)-γ-phenyl(1,1'-biphenyl)-4-propanol methanesulfonate (ester) (interm. 21).

EXAMPLE A.6

A mixture of ((1,1'-biphenyl)-4-yl)phenylmethanone (0.01 mol) in THF (200 ml) was stirred at room temperature under $N_2$ flow. Vinylmagnesium chloride (0.011 mol; 1M solution in THF) was added dropwise. The mixture was stirred at room temperature for 1 hour. HCl (150 ml) was added. The mixture was stirred at room temperature for 1 hour and extracted with DIPE. The organic layer was separated, washed once with a saturated $K_2CO_3$ solution, twice with $H_2O$ and once with a saturated NaCl solution, then dried, filtered and the solvent was evaporated. This fraction was purified by column chromatography over silica gel (eluent: $CH_2Cl_2$hexane/EtOAc 50/30/20). Two pure fractions were collected and their solvents were evaporated, yielding 8.8 g (29%) of 4-(3-chloro-1-phenyl-1-propenyl) (1,1'-biphenyl) (interm. 22).

EXAMPLE A.7 a) A mixture of bromobenzene (0.3 mol) in THF (300 ml) was added dropwise to a mixture of magnesium (0.32 mol) in THF (20 ml). The mixture was stirred and refluxed for 1 hour. A mixture of 4-biphenylcarboxaldehyde (0.3 mol) in THF (500 ml) was added dropwise. The mixture was stirred and refluxed for 2 hours, at room temperature overnight, poured out into a saturated $NH_4Cl$ solution and extracted with DCM. The organic layer was separated, washed three times, dried, filtered and the solvent was evaporated. The residue was triturated in hexane, filtered off and purified over silica gel on a glass filter (eluent: $CH_2Cl_2$ 100%). The pure fractions were collected and the solvent was evaporated. The residue was triturated in DIPE, filtered off and dried, yielding 31 g of (±)-α-phenyl(1,1'-biphenyl)-4-methanol (interm. 23).

b) A mixture of intermediate (23) (0.08 mol) in hydrochloric acid (50 ml) and DCM (200 ml) was stirred at room temperature overnight. The organic layer was separated, washed, dried, filtered and the solvent was evaporated. The residue was crystallized from hexane. The precipitate was filtered off and dried, yielding 20 g of (±)-4-(chlorophenylmethyl)(1,1'-biphenyl) (interm. 24).

EXAMPLE A.8

Intermediate (16) was converted into the free base and acrylonitrile (0.02 mol) in methanol (50 ml) was stirred and refluxed overnight. Acrylonitrile (0.09 mol) was added. The mixture was stirred and refluxed overnight. $K_2CO_3$ was added. The mixture was stirred and refluxed for 2 hours. The solvent was evaporated. The residue was dissolved in DCM. The organic solution was washed, dried, filtered and the solvent was evaporated. The residue was purified by column chromatography over silica gel (eluent: $CH_2Cl_2/CH_3OH$ 98/2). The pure fractions were collected and the solvent was evaporated. The residue was crystallized from 2-propanol. The precipitate was filtered off and dried, yielding 1.8 g of (A)-4-[([1,1'-biphenyl]-4-yl)phenylmethyl]-1-piperidinepropanenitrile (interm. 25, $[\alpha]_D^{20}$=−8.29° (c=24.73 mg/5 ml in DMF), mp. 106° C.). Analogously but starting from intermediate (26), (B)-4-[([1,1'-biphenyl]-4-yl)-phenylmethyl]-1-piperidinepropanenitrile (interm. 27,$[\alpha]_D^{20}$=+8.23° (c=24.923 mg/5 ml in DMF), mp. 92° C.), was prepared.

B. Preparation of the Final Compounds

EXAMPLE B.1

A mixture of intermediate (2) (0.06 mol) in hydrobromic acid (48%) (250 ml) was stirred and refluxed for 4 hours and then cooled. The precipitate was filtered off and dried, yielding 25.2 g of product. Part of this fraction (5 g) was converted into the free base and purified by column chromatography over silica gel (eluent: $CH_2Cl_2/CH_3OH$ 95/5). The pure fractions were collected and the solvent was evaporated. The residue was dissolved in 2-propanol and converted into the hydrochloric acid salt (1:2) from 2-propanol/HCl. The precipitate was filtered off and dried, yielding 4.2 g of 4-[[(1,1'-biphenyl)-4-yl](4-fluorophenyl)methylen](1,4'-bipiperidine)dihydrochloride 2-propanolate (1:1) (comp. 2).

EXAMPLE B.2

A mixture of intermediate (8) (0.051 mol) and potassium hydroxide (40 g) in 2-propanol (400 ml) was stirred and refluxed for 5 hours. The mixture was cooled and the solvent was evaporated. The residue was dissolved in $H_2O$ (500 ml) and extracted three times with DCM. The combined organic layer was washed once with $NH_4Cl$ (10%), twice with $H_2O$ and once with a saturated NaCl solution, then dried, filtered and the solvent was evaporated, yielding 19 g (87%) of 4-[[4'-fluoro-(1,1'-biphenyl)-4-yl]phenyl-methylene](1,4'-bipiperidine)(comp. 4).

EXAMPLE B.3

A mixture of compound (4) (0.029 mol) in acetic acid (250 ml) was hydrogenated at 20° C. with palladium on activated carbon (2 g) as a catalyst. After uptake of hydrogen (1 eq.), the catalyst was filtered off and the filtrate was evaporated. A saturated $K_2CO3$ solution (100 ml) was added. The mixture was extracted three times with DCM. The combined organic layer was washed twice with $H_2O$ and once with a saturated NaCl solution, dried, filtered and the solvent was evaporated. This fraction was purified by column chromatography over silica gel (eluent: $CH_2Cl_2$/($CH_3OH/NH_3$) 95/5). Two pure fractions were collected and their solvents were evaporated, yielding 3.5 g of fraction 1 and 3.5 g of fraction 2. Fraction 2 was converted into the hydrochloric acid salt (1:2) from 2-propanol/HCl. The precipitate was filtered off and dried, yielding (±)-4-[[4'-fluoro (1,1'-biphenyl)-4-yl]phenylmethyl](1,4'-bipiperidine) dihydro-chloride.monohydrate (comp. 7).

EXAMPLE B.4

A mixture of ethyl 4-[[(1,1'-biphenyl)-4-yl]phenylmethylene](1,4'-bipiperidine)-1'-carboxylate (0.0083 mol) in methanol (150 ml) was hydrogenated with palladium on carbon (10%, 2 g) as a catalyst. After uptake of hydrogen (1 equivalent), the catalyst was filtered off and the filtrate was evaporated. A mixture of potassium hydroxide (20 g) in 2-propanol (200 ml) was added to the residue The mixture was stirred and refluxed for 4 hours. The solvent was evaporated. The residue was dissolved in DCM (500 ml). The mixture was washed three times with $H_2O$ and once with a saturated NaCl solution, dried, filtered and the solvent was evaporated. The residue was converted into the hydrochloric acid salt (1:2) with 2-propanol/HCl. The precipitate was filtered off and dried, yielding 2.7 g (69.7%) of (±)-4-[[(1,1'-biphenyl)-4-yl]phenylmethyl](1,4'-bipiperidine) dihydrochloride monohydrate (comp. 20).

EXAMPLE B.5

Palladium or platinum on actived carbon (0.100 g, as a catalyst) was stirred in methanol (2 ml), under $N_2$ atmosphere. A solution of thiophene in methanol (1 ml) was added. Potassium acetate (0.100 g) was added. Butanal (0.100 g, ±0.0003 mol) was added. Compound (20) (0.0003 mol) in methanol (3 ml) was added and the reaction mixture was hydrogenated over the weekend at 50° C. After uptake of hydrogen (1 equivalent), the catalyst was filtered off. The desired compound was isolated and purified by high-performance liquid chromatography over a Prochrom D.A.C.-column (I.D.: 5 cm) with Kromasil Spherical silica Si60 (100 g, 5 μm; eluent gradient: $CH_2Cl_2$/($CH_2Cl_2$/$CH_3OH$ 9/1)/$CH_3OH$ (0 min) 100/0/0, (10.31 min) 0/100/0,(10.32 min) 50/0/50, (13.02 min) 0/0/100, (13.33–18.32 min) 100/0/0). The desired fractions were collected and the solvent was evaporated, yielding 0.040 g of (±)-4-[[(1,1'-biphenyl)-4-yl]phenyl-methyl]-1 '-butyl(1,4'-bipiperidine) (comp. 14).

EXAMPLE B.6

A mixture of intermediate (21) (0.00027 mol), N,N,N'-trimethyl-1,3-propanediamine (0.100 g) and sodium carbonate (0.100 g) in N,N-dimethylformamide (1 ml) was stirred overnight at 90° C. The desired compound was isolated and purified by high-performance liquid chromatography over Hyperprep 'BDS' HS C18 (55 g, 8 μm, 100 Å; eluent gradient: [(0.5% $NH_4OAc$ in $H_2O$)/$CH_3CN$ 90/10]/$CH_3OH$/$CH_3CN$ (0 min) 75/25/0, (10.31 min) 0/50/50, (16.32 min) 0/0/100, (16.33 min-end) 75/25/0). The desired fractions were collected and the solvent was evaporated, yielding 0.020 g of (±)-N-[3-[(1,1'-biphenyl)-4-yl]-3-phenylpropyl]-N,N',N'-trimethylpropanediamine (comp. 38).

EXAMPLE B.7

A mixture of N,N'-dimethyl-N-[(3-methylamino)propyl]-1,3-propanediamine (0.0248 mol) in DMF (75 ml) was stirred at 60° C. A mixture of intermediate (24) (0.01 mol) in DMF (75 ml) was added dropwise. The mixture was stirred at 60° C. for 6 hours and at room temperature overnight. The solvent was evaporated. $H_2O$ (100 ml) was added and the mixture was extracted three times with DCM. The combined organic layer was washed twice with $H_2O$ and once with a saturated NaCl solution, then dried, filtered and the solvent was evaporated. The residue was purified by HPLC over silica gel (eluent: $CH_2Cl_2/CH_3OH/(CH_3OH/NH_3)$ 92/4/4). The pure fractions were collected and the solvent was evaporated. The residue was converted into the hydrochloric acid salt (1:3) with 2-propanol/HCl. The precipitate was filtered off and dried, yielding (±)-N-[[(1,1'-biphenyl)4-yl]phenylmethyl]-N,N'-dimethyl-N'-[3-(methylamino)propyl]-1,3-propanediamine trihydrochloride (comp. 52).

EXAMPLE B.8

The Grignard reaction was started with magnesium (0.08 mol) and a few ml of a mixture of 4-bromobiphenyl (0.08 mol) in THF (150 ml). Then the rest of the mixture of 4-bromobiphenyl in THF was added dropwise. The resulting reaction mixture was stirred and refluxed for 1 hour and then cooled. 1-(2,4-dichlorophenyl)-3-[4-[2-(dimethylamino)ethyl]-1-piperidinyl]-1-propanone dihydrochloride (0.023 mol) dissolved in diethyl ether (50 ml) was added dropwise. The mixture was stirred and refluxed for 1 hour, then cooled, decomposed with $NH_4Cl$ 10% and stirred. A diluted aqueous HCl solution was added. The mixture was stirred for a while. The organic layer was separated, washed with $H_2O$, dried and filtered. The filtrate was saturated with HCl/2-propanol. The precipitate was filtered off and crystallized from $CH_3OH$ and diethyl ether. The precipitate was filtered off and dried, yielding 1.05 g (7.8%) of (±)-α-[(1,1'-biphenyl)-4-yl]-a-(2,4-dichlorophenyl)-4-[2-(dimethylamino)ethyl]-1-piperidine-propanol dihydrochloride (comp. 34).

EXAMPLE B.9

A mixture of (±)-N-[3-([1,1'-biphenyl]-4-yl)-3-phenylpropyl]-N'-methyl-N'-(phenylmethyl)-1,2-ethanediamine (0.006 mol) in methanol (150 ml) was hydrogenated at room temperature with palladium on carbon (10%, 1 g) as a catalyst. After uptake of hydrogen (1 equivalent), the catalyst was filtered off and the filtrate was evaporated, giving a residue that was converted into the hydrochloric acid salt (1:2) with HCl/2-propanol, yielding 2.76 g of (±)-N-[3-([1,1'-biphenyl]-4-yl)-3-phenylpropyl]-N'-methyl-1,2-ethanediamine dihydrochloride (comp. 56).

EXAMPLE B.10

A mixture of intermediate (25) (0.003 mol) in a mixture of methanol saturated with $NH_3$ (200 ml) was hydrogenated at 20° C. overnight with Raney Ni (1 g) as a catalyst. After uptake of hydrogen (2 equivalents), the catalyst was filtered off and the filtrate was evaporated. The residue was dissolved in 2-propanol and converted into the hydrochloric acid salt (1:2) with 2-propanol/HCl. The solvent was evaporated. The residue was triturated in diethyl ether, filtered off and dried, yielding 1.4 g of (A)-4 -[([1,1'-biphenyl]-4-yl)phenylmethyl]-1-piperidinepropanamine dihydrochloride tetrahydrate (comp. 78).

Table F-1 to F-5 list the compounds that were prepared according to one of the above Examples. The following abbreviations were used in the tables: . $C_4H_6O_5$ stands for the 2-hydroxybutanedioic acid salt (malic acid salt), .$C_2H_2O_4$ stands for the ethanedioate salt, .$C_4H_6O_4$ stands for the butanedioate salt, .$C_4H_6O_6$ stands for the [R-(R*,R*)]-2,3-dihydroxy-butanedioic acid salt (L-tartaric acid salt), .(E)-$C_4H_4O_4$ stands for (E)-2-butenedioic acid salt (fumaric acid salt),.(Z)-$C_4H_4O_4$ stands for (Z)-2-butenedioic acid salt (maleic acid salt), .$C_6H_8O_7$ stands for .2-hydroxy-1,2,3-propanetricarboxylate (citric acid salt), and BIT stands for the 1,2-benzisothiazolin-3-one salt.

TABLE F-1

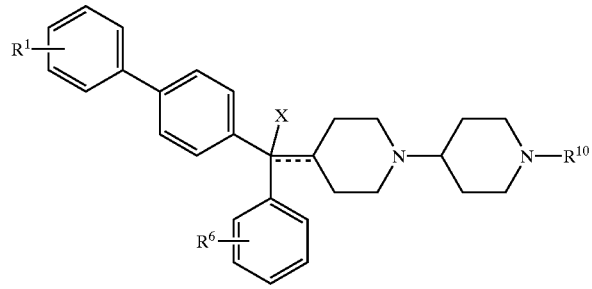

| Co No. | Ex. No. | X | ----- | $R^1$ | $R^6$ | $R^{10}$ | physical data |
|---|---|---|---|---|---|---|---|
| 1 | B.2 | d.b. | double | 4-F | 4-F | H | .(E)-$C_4H_4O_4$ (1:2) |
| 2 | B.1 | d.b. | double | H | 4-F | H | .HCl (1:2) .2-propanolate (1:1) |
| 3 | B.1 | d.b. | double | H | H | H | .HCl (1:2) |
| 4 | B.2 | d.b. | double | 4-F | H | H | — |
| 5 | B.2 | d.b. | double | 4-F | H | H | .HCl (1:1) .$H_2O$ (1:1) |
| 6 | B.2 | H | single | 4-F | 4-F | H | .HCl (1:2) |
| 7 | B.3 | H | single | 4-F | H | H | .HCl (1:2) .$H_2O$ (1:1) |
| 8 | B.2 | H | single | 4-F | 4-Cl | H | .HCl (1:2) |
| 9 | B.2 | H | single | 4-F | 4-$CH_3$ | H | .HCl (1:2) |

TABLE F-1-continued

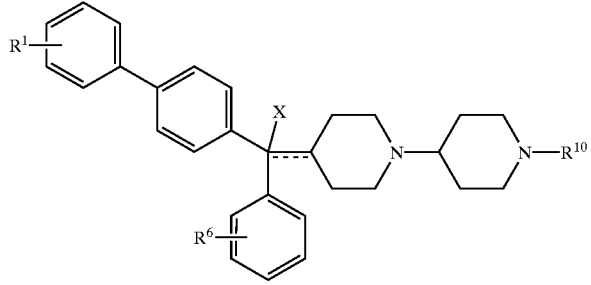

| Co No. | Ex. No. | X | ----- | R¹ | R⁶ | R¹⁰ | physical data |
|---|---|---|---|---|---|---|---|
| 10 | B.1 | H | single | 4-SO₂OH | 4-SO₂OH | H | — |
| 11 | B.4 | H | single | H | 4-F | H | .HCl (1:1) .H₂O (1:2) |
| 12 | B.1 | H | single | H | 4-OCH₃ | H | .HBr (1:2) |
| 13 | B.1 | H | single | H | 4-OH | H | .HCl (1:2) .H₂O (1:3) |
| 14 | B.5 | H | single | H | H | (CH₂)₃CH₃ | — |
| 15 | B.5 | H | single | H | H | (CH₂)₃N(CH₃)₂ | .HCl (1:3) .H₂O (1:5) |
| 16 | B.4 | H | single | H | H | (CH₂)₃NH₂ | .H₂O (1:1) |
| 17 | B.5 | H | single | H | H | (CH₂)₉CH₃ | — |
| 18 | B.5 | H | single | H | H | CH₂CH₃ | .HCl (1:2) |
| 19 | B.5 | H | single | H | H | CH₃ | — |
| 20 | B.4 | H | single | H | H | H | .HCl (1:2) .H₂O (1:1) |
| 21 | B.1 | H | single | H | H | H | .HBr (1:2) |
| 22 | B.1 | H | single | H | H | H | (A); .HCl (1:2) .H₂O (1:1) [α]²⁰_D + 5.08° (c = 0.05% in CH₃OH) |
| 23 | B.1 | H | single | H | H | H | (B); .HCl (1:2) .H₂O (1:1) [α]²⁰_D = −2.14° (c = 0.05% in CH₃OH) | d.b.: direct bond

TABLE F-2

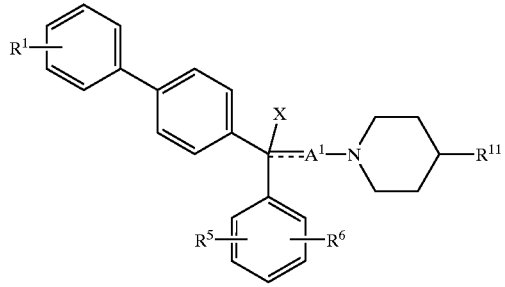

| Co No. | Ex. No. | X | -----A¹ | R¹ | R⁵ | R⁶ | R¹¹ | physical data |
|---|---|---|---|---|---|---|---|---|
| 24 | B.7 | d.b. | =CH—CH₂ | H | H | H | —(CH₂)₂N(CH₃)₂ | .HCl (1:2) |
| 25 | B.1 | d.b. | =CH—CH₂ | H | H | H | —(CH₂)₂NH₂ | .(COOH)₂ (1:2) |
| 26 | B.1 | d.b. | =CH—CH₂ | H | H | H | —CH₂NH₂ | .(COOH)₂ (1:2) .H₂O (1:1) |
| 27 | B.1 | d.b. | =CH—CH₂ | H | H | H | NH₂ | .(COOH)₂ (1:2) .H₂O (1:1) |
| 28 | B.4 | H | —(CH₂)₂ | H | H | H | —(CH₂)₂N(CH₃)₂ | .HCl (1:2) |
| 29 | B.1 | H | —(CH₂)₂ | H | H | H | —(CH₂)₂NH₂ | .HCl (1:2) .2-propanolate (1:1) |
| 30 | B.1 | H | —(CH₂)₂ | H | H | H | —CH₂NH₂ | .HCl (1:2) .2-propanolate (1:1) |
| 31 | B.1 | H | —(CH₂)₂ | H | H | H | —NH₂ | .HCl (1:2) .2-propanolate (1:1) |
| 32 | B.7 | H | —(CH₂)₂ | H | H | H | —N(CH₃)₂ | — |
| 33 | B.7 | H | —(CH₂)₂ | H | H | H | —CH₂N(CH₃)₂ | — |

TABLE F-2-continued

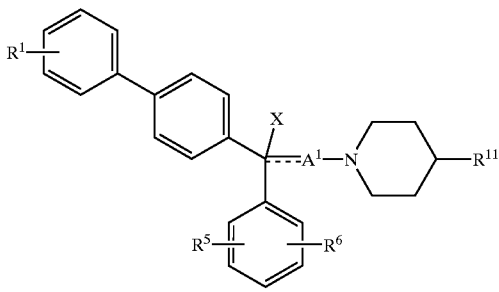

| Co No. | Ex. No. | X | ----A¹ | R¹ | R⁵ | R⁶ | R¹¹ | physical data |
|---|---|---|---|---|---|---|---|---|
| 34 | B.8 | OH | —(CH₂)₂— | H | 2-Cl | 4-Cl | —(CH₂)₂N(CH₃)₂ | .HCl (1:2) |
| 55 | B.6 | d.b. | =CH—CH₂— | H | H | H | —N(CH₃)₂ | — |

TABLE F-3

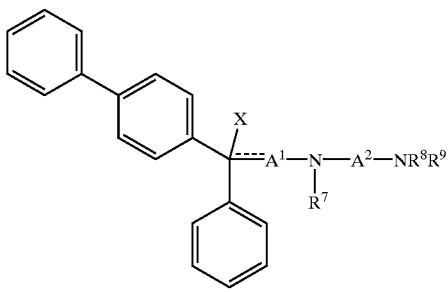

| Co No. | Ex. No. | X | ----A¹ | R⁷ | —A²—NR⁸R⁹ | physical data |
|---|---|---|---|---|---|---|
| 35 | B.7 | d.b. | =CH—CH₂— | CH₃ | —(CH₂)₃N(CH₃)₂ | — |
| 36 | B.7 | d.b. | =CH—CH₂— | H | —(CH₂)₃N(CH₃)₂ | — |
| 37 | B.7 | d.b. | =CH—CH₂— | H | —(CH₂)₂N(CH₃)₂ | — |
| 38 | B.6 | H | —CH₂—CH₂— | CH₃ | —(CH₂)₃N(CH₃)₂ | — |
| 39 | B.6 | H | —CH₂—CH₂— | H | —(CH₂)₃N(CH₃)₂ | — |
| 40 | B.4 | H | —CH₂—CH₂— | H | —(CH₂)₃NH₂ | .HCl (1:2) |
| 56 | B.9 | H | —CH₂—CH₂— | H | —(CH₂)₂NH(CH₃) | .HCl (1:2) |
| 57 | B.9 | H | —CH₂—CH₂— | H | —(CH₂)₂NH₂ | .HCl (1:2) |
| 58 | B.9 | H | —CH₂—CH₂— | H | —(CH₂)₃NH(CH₃) | .HCl (1:2) |
| 59 | B.9 | H | —CH₂—CH₂— | H | —(CH₂)₃NH₂ | — |
| 60 | B.9 | H | —CH₂—CH₂— | CH₃ | —(CH₂)₃NH(CH₃) | .(COOH)₂ (1:2) |
| 61 | B.10 | H | —CH₂—CH₂— | CH₃ | —(CH₂)₃NH₂ | .(COOH)₂ (2:5) .H₂O (1:1) |
| 62 | B.1 | H | —CH₂—CH₂— | H | —(CH₂)₄NH₂ | .HCl (1:2) |
| 63 | B.9 | H | —CH₂—CH₂— | H | —(CH₂)₃NH₂ | .C₄H₆O₄ (1:2) |
| 64 | B.9 | H | —CH₂—CH₂— | H | —(CH₂)₃NH₂ | .(E)-C₄H₄O₄ (1:2) |
| 65 | B.9 | H | —CH₂—CH₂— | H | —(CH₂)₃NH₂ | .(COOH)₂ (1:2) |
| 66 | B.9 | H | —CH₂—CH₂— | H | —(CH₂)₃NH₂ | .4-methylbenzene-sulfonate (1:2) |
| 67 | B.9 | H | —CH₂—CH₂— | H | —(CH₂)₃NH₂ | .sulfamate (1:2) |
| 68 | B.9 | H | —CH₂—CH₂— | H | —(CH₂)₃NH₂ | .C₆H₈O₇ (3:4) |
| 69 | B.9 | H | —CH₂—CH₂— | H | —(CH₂)₃NH₂ | (+)-; .C₄H₆O₆ (2:3) |
| 70 | B.9 | H | —CH₂—CH₂— | H | —(CH₂)₃NH₂ | .H₂SO₄ (2:3) .H₂O (1:1) |
| 71 | B.9 | H | —CH₂—CH₂— | CH₃ | —(CH₂)₂NH(CH₃) | .HCl (1:1) |
| 72 | B.9 | H | —CH₂—CH₂— | CH₃ | —(CH₂)₂NH₂ | .(COOH)₂ (1:2) |
| 73 | B.9 | H | —CH₂—CH₂— | CH₃ | —(CH₂)₂NH₂ | .BIT (1:1) |
| 74 | B.9 | H | —CH₂—CH₂— | CH₃ | —(CH₂)₂NH₂ | .BIT (1:2) |
| 75 | B.9 | H | —CH₂—CH₂— | H | —(CH₂)₃NH₂ | (A); .HCl (1:2); mp. 260° C.; $[\alpha]^{20}_D = -8.83°$ (c = 18.68 mg/5 ml in DMF) |

TABLE F-3-continued

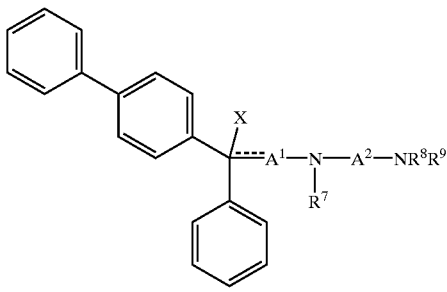

| Co No. | Ex. No. | X | =A¹ | R⁷ | —A²—NR⁸R⁹ | physical data |
|---|---|---|---|---|---|---|
| 76 | B.9 | H | —CH₂—CH₂— | H | —(CH₂)₃NH₂ | (B); .HCl (1:2); [α] = +7.77° (c = 19.31 mg/5 ml in DMF) |
| 77 | B.9 | H | —(CH₂)₃— | H | —(CH₂)₃NH₂ | .HCl (2:1) |

TABLE F-4

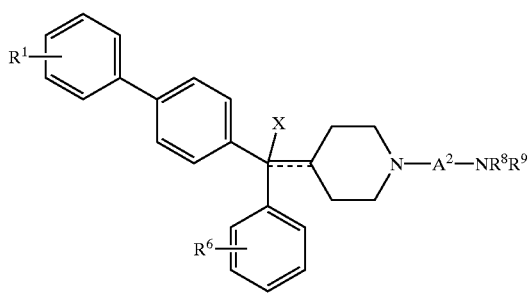

| Co No. | Ex. No. | X | ===== | R¹ | R⁶ | —A²—NR⁸R⁹ | physical data |
|---|---|---|---|---|---|---|---|
| 41 | B.4 | H | single | H | H | —(CH₂)₃NH₂ | — |
| 42 | B.4 | H | single | H | H | —(CH₂)₃NH₂ | .HCl (1:2) .H₂O (1:1) |
| 43 | B.5 | H | single | H | H | —(CH₂)₃N(CH₃)₂ | .HCl (1:2) |
| 78 | B.10 | H | single | H | H | —(CH₂)₃NH₂ | (A); .HCl (1:2) .H₂O (1:4) |
| 79 | B.10 | H | single | H | H | —(CH₂)₃NH₂ | (B); .HCl (1:2) .H₂O (1:1) |
| 80 | B.4 | H | single | H | H | —(CH₂)₃NH₂ | .C₄H₆O₄ (1:2) |
| 81 | B.4 | H | single | H | H | —(CH₂)₃NH₂ | (E)-C₄H₄O₄ (2:3) |
| 82 | B.4 | H | single | H | H | —(CH₂)₃NH₂ | .(COOH)₂ (1:2) .H₂O (1:1) |
| 83 | B.4 | H | single | H | H | —(CH₂)₃NH₂ | .C₆H₈O₇ (3:5) .H₂O (1:1) .2-propanolate (1:1) |
| 84 | B.4 | H | single | H | H | —(CH₂)₃NH₂ | (+)-.C₄H₆O₆ (2:3) .H₂O (1:1) |
| 85 | B.4 | H | single | H | H | —(CH₂)₃NH₂ | .H₂SO₄ (2:3) |
| 86 | B.10 | H | single | H | H | —(CH₂)₂NH₂ | .HCl (1:2) .H₂O (1:1) |
| 87 | B.4 | H | single | H | H | —(CH₂)₃NH₂ | .BIT (1:1) |
| 88 | B.4 | H | single | H | H | —(CH₂)₃NH₂ | .BIT (1:2) |

55

TABLE F-5

| Co No. | Ex. No. | X | ----L | physical data |
|---|---|---|---|---|
| 44 | B.1 | H | methyl-piperidine-N-piperidine-N-piperidine-NH | .HCl (1:3) .H₂O (1:1) .2-propanolate (1:1) |
| 45 | B.7 | H | methyl-piperidine-N-piperidine | .HCl (1:1) |
| 46 | B.2 | H | methyl-piperazine-N-piperidine-NH | .HCl (1:3) |
| 47 | B.2 | H | CH₃NH-piperidine-N-piperidine-NH | — |
| 48 | B.2 | H | (CH₃)₂N-piperidine-N-piperidine-NH | .H₂O (1:2) |
| 49 | B.1 | H | methyl-N-piperidine-N-piperidine-NH₂ | .HCl (1:3) |
| 50 | B.1 | H | —(CH₂)₂—NH—piperidine-NH | .HBr (1:2) |
| 51 | B.1 | H | —(CH₂)₂—N(CH₃)—piperidine-NH | .HBr (1:2) |
| 52 | B.7 | H | CH₃N(CH₃)—(CH₂)₃—N(CH₃)—(CH₂)₃—NHCH₃ | .HCl (1:3) |
| 53 | B.7 | H | CH₃NH—(CH₂)₃—N(CH₃)—(CH₂)₃—NH₂ | .C₂H₂O₄ (1:3) |
| 54 | B.5 | H | (CH₃)₂N—(CH₂)₃—N(CH₃)—(CH₂)₃—N(CH₃)₂ | .HCl (1:3) .H₂O (1:1) |
| 89 | B.1 | H | —(CH₂)₂—N-piperidine-N(CH₃)-piperidine-NH | .HCl (1:3) .H₂O (1:3) |
| 90 | B.9 | H | —(CH₂)₂—N-piperidine-NH-piperidine-NH | .HCl (1:3) .H₂O (1:1) |

TABLE F-5-continued

| Co No. | Ex No. | X | ----L | physical data |
|---|---|---|---|---|
| 91 | | H | (propyl-NH-CH₂CH₂CH₂-N⁺(CH₃)₃ I⁻) | — |
| 92 | | H | (1-methyl-4-piperidinyl-N⁺-CH₂CH₂-NH₂ I⁻) | — |

C. Biological Examples

C.1. Primary Bacteria Screening

The stock solutions with the test compounds were pipetted into multiwell plates and mixed with warm tryptose broth agar (2.6%) in order to reach a test compound concentration of 500 μMol. The medium was allowed to cool and subsequently inoculated with the bacteria. Wells were placed in an incubator at 27° C. and a relative humidity of 70%. After sufficient growth of the untreated cultures, the test was evaluated.

Test Bacteria

*Pseudomonas aeruginosa*

*Escherichia coli*

15 Score system:

3: complete inhibition of bacterial growth

2: bacterial growth partially controlled

1: bacterial growth comparable to untreated

TABLE C.1

| Co. No. | E. coli | P. aeruginosa | Co. No. | E. coli | P. aeruginosa |
|---|---|---|---|---|---|
| 1 | 3 | 1 | 38 | 1 | 1 |
| 2 | 3 | 1 | 39 | 3 | 1 |
| 3 | 1 | 1 | 40 | 3 | 3 |
| 5 | 2 | 1 | 42 | 3 | 3 |
| 6 | 3 | 3 | 43 | 1 | 2 |
| 7 | 3 | 3 | 44 | 3 | 1 |
| 8 | 3 | 3 | 45 | 1 | 1 |
| 9 | 3 | 2 | 46 | 1 | 3 |
| 10 | 1 | 1 | 47 | 3 | 1 |
| 11 | 3 | 3 | 48 | 1 | 1 |
| 12 | 3 | 2 | 49 | 3 | 1 |
| 13 | 3 | 3 | 50 | 3 | 1 |
| 14 | 1 | 3 | 51 | 3 | 1 |
| 15 | 1 | 1 | 52 | 3 | 1 |
| 16 | 3 | 3 | 53 | 3 | 1 |
| 18 | 1 | 2 | 54 | 3 | 1 |
| 19 | 1 | 1 | 56 | 3 | 1 |
| 20 | 3 | 3 | 63 | 3 | 3 |
| 22 | 3 | 1 | 64 | 3 | 3 |
| 23 | 1 | 3 | 65 | 3 | 3 |
| 24 | 1 | 1 | 66 | 3 | 3 |
| 25 | 3 | 1 | 67 | 3 | 2 |
| 26 | 3 | 1 | 68 | 3 | 1 |
| 27 | 3 | 1 | 69 | 3 | 1 |
| 28 | 1 | 1 | 70 | 3 | 1 |

TABLE C.1-continued

| Co. No. | E. coli | P. aeruginosa | Co. No. | E. coli | P. aeruginosa |
|---|---|---|---|---|---|
| 29 | 3 | 1 | 73 | 3 | 3 |
| 30 | 3 | 1 | 78 | 3 | 3 |
| 31 | 3 | 1 | 81 | 3 | 3 |
| 32 | 1 | 1 | 82 | 3 | 3 |
| 33 | 1 | 1 | 83 | 3 | 3 |
| 34 | 1 | 1 | 84 | 3 | 3 |
| 35 | 3 | 1 | 85 | 3 | 3 |
| 36 | 1 | 1 | 89 | 3 | 1 |
| 37 | 1 | 1 | | | |

C.2. Secondary Bacteria Screening

A number of compounds of formula (I) were also tested in a secondary screening against a wide variety of bacteria. The test conditions are the same as described in biological C.1. The concentration of the test compound was also 500 μmol, and the scoring system used was also the same.

Test Bacteria

| Bacteria | No. | Bacteria | No. |
|---|---|---|---|
| *Pseudomonas alcaligenes* | 1 | *Pseudomanas testosteroni* | 10 |
| *Bacillus cereus mycoides* | 2 | *Brevibacterium ammoniagenes* | 11 |
| *Flavobacterium sp.* | 3 | *Cellulomonas flavigena* | 12 |
| *Steptomyces albus* | 4 | *Corynebacterium oortii* | 13 |
| *Shewanella putrefaciens* | 5 | *Pseudomonas stutzeri* | 14 |
| *Pseudomonas fluorescens* | 6 | *Proteus vulgaris* | 15 |
| *Pseudomonas oleovorans* | 7 | *Klebsiella pneumoniae* | 16 |
| *Alcaligenes faecalis* | 8 | *Providencia rettgeri* | 17 |
| *Citrobacter freundii* | 9 | *Pseudomonas putida* | 18 |

TABLE C.2

| Co. No. | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 6 | 3 | 3 | 3 | 3 | 2 | 3 | 3 | 1 | 3 | 3 | 3 | 2 | 3 | 3 | 2 | 2 | 2 | 3 |
| 7 | 3 | 3 | 3 | 3 | 2 | 3 | 3 | 1 | 3 | 3 | 3 | 2 | 3 | 3 | 2 | 3 | 2 | 3 |
| 9 | 3 | 3 | 3 | 3 | 1 | 3 | 3 | 1 | 3 | 3 | 3 | 1 | 3 | 3 | 1 | 3 | 1 | 2 |
| 11 | 3 | 3 | 3 | 3 | 2 | 3 | 3 | 1 | 3 | 3 | 3 | 2 | 3 | 3 | 2 | 3 | 2 | 2 |
| 12 | 3 | 3 | 3 | 3 | 1 | 3 | 3 | 2 | 3 | 3 | 3 | 1 | 3 | 3 | 1 | 3 | 1 | 3 |
| 13 | 3 | 3 | 3 | 3 | 1 | 3 | 3 | 1 | 3 | 3 | 3 | 1 | 3 | 3 | 1 | 1 | 1 | 3 |
| 16 | 3 | 3 | 3 | 3 | 1 | 3 | 3 | 1 | 3 | 3 | 3 | 1 | 3 | 3 | 1 | 1 | 1 | 3 |
| 18 | 3 | 3 | 3 | 3 | 1 | 3 | 3 | 1 | 1 | 3 | 3 | 1 | 3 | 3 | 1 | 1 | 1 | 1 |
| 20 | 3 | 3 | 3 | 3 | 2 | 3 | 3 | 1 | 3 | 3 | 3 | 2 | 3 | 3 | 2 | 3 | 2 | 3 |
| 22 | 3 | 3 | 3 | 3 | 1 | 2 | 3 | 1 | 3 | 3 | 3 | 1 | 3 | 3 | 1 | 3 | 1 | 2 |
| 23 | 3 | 3 | 3 | 3 | 1 | 3 | 3 | 1 | 3 | 3 | 3 | 1 | 3 | 3 | 1 | 3 | 1 | 3 |
| 25 | 3 | 3 | 3 | 3 | 1 | 1 | 3 | 1 | 3 | 3 | 3 | 1 | 3 | 3 | 1 | 2 | 1 | 3 |
| 26 | 3 | 3 | 3 | 3 | 1 | 1 | 3 | 1 | 3 | 3 | 3 | 1 | 3 | 3 | 1 | 3 | 1 | 3 |
| 27 | 3 | 3 | 3 | 3 | 1 | 1 | 3 | 1 | 3 | 3 | 3 | 1 | 3 | 3 | 1 | 3 | 1 | 3 |
| 29 | 3 | 3 | 3 | 3 | 1 | 1 | 3 | 1 | 3 | 3 | 3 | 1 | 3 | 3 | 1 | 1 | 1 | 3 |
| 30 | 3 | 3 | 3 | 3 | 1 | 1 | 3 | 1 | 3 | 3 | 3 | 1 | 3 | 3 | 1 | 3 | 1 | 3 |
| 31 | 3 | 3 | 3 | 3 | 1 | 1 | 3 | 2 | 3 | 3 | 3 | 1 | 3 | 3 | 1 | 3 | 1 | 3 |
| 33 | 3 | 3 | 3 | 3 | 2 | 2 | 2 | 1 | 3 | 3 | 3 | 2 | 3 | 3 | 2 | 2 | 2 | 2 |
| 39 | 3 | 3 | 3 | 3 | 2 | 1 | 2 | 1 | 3 | 3 | 3 | 2 | 3 | 3 | 2 | 3 | 2 | 1 |
| 40 | 3 | 3 | 3 | 3 | 3 | 3 | 3 | 3 | 3 | 3 | 3 | 2 | 3 | 3 | 2 | 3 | 2 | 3 |
| 42 | 3 | 3 | 3 | 3 | 2 | 3 | 3 | 2 | 3 | 3 | 3 | 2 | 3 | 3 | 2 | 3 | 2 | 3 |
| 43 | 3 | 3 | 3 | 3 | 2 | 3 | 3 | 1 | 3 | 3 | 3 | 2 | 3 | 3 | 2 | 2 | 2 | 2 |
| 46 | 3 | 3 | 3 | 3 | 1 | 3 | 1 | 1 | 1 | 3 | 3 | 1 | 3 | 3 | 1 | 1 | 1 | 1 |
| 47 | 3 | 3 | 3 | 3 | 1 | 1 | 3 | 1 | 3 | 3 | 3 | 1 | 3 | 3 | 1 | 3 | 1 | 3 |
| 49 | 3 | 3 | 3 | 3 | 2 | 3 | 3 | 1 | 3 | 3 | 3 | 2 | 3 | 3 | 2 | 3 | 2 | 3 |
| 50 | 3 | 3 | 3 | 3 | 2 | 2 | 3 | 3 | 3 | 3 | 3 | 2 | 3 | 3 | 2 | 3 | 2 | 3 |
| 51 | 3 | 3 | 3 | 3 | 2 | 2 | 3 | 1 | 3 | 3 | 3 | 2 | 3 | 3 | 2 | 3 | 2 | 3 |
| 52 | 3 | 3 | 3 | 3 | 2 | 2 | 3 | 1 | 3 | 3 | 3 | 2 | 3 | 3 | 2 | 3 | 2 | 3 |

C.3. Screening Against Yeasts

A number of compounds of formula (I) were also tested in a screening against certain The test conditions are the same as described in biological example C.1. The concentration of the test compound was also 500 μmol, and the scoring system used was also the same.

Test Yeast

*Debaryomyces hansenii* (19)

*Rhodotorula rubra* (20)

*Sporobolomyces roseus* (21)

TABLE C.3

| Co. No. | Test yeast (19) | (20) | (21) |
|---|---|---|---|
| 6 | 3 | 3 | 3 |
| 7 | 3 | 2 | 3 |
| 9 | 3 | 3 | 3 |
| 11 | 3 | 1 | 3 |
| 12 | 3 | 2 | 3 |
| 13 | 3 | 1 | 3 |
| 16 | 3 | 3 | 3 |
| 18 | 3 | 1 | 3 |
| 20 | 3 | 3 | 3 |
| 22 | 3 | 1 | 3 |
| 23 | 3 | 3 | 3 |
| 25 | 3 | 1 | 3 |
| 26 | 3 | 2 | 3 |
| 27 | 3 | 1 | 3 |
| 29 | 3 | 3 | 3 |
| 30 | 3 | 1 | 3 |
| 31 | 3 | 1 | 3 |
| 33 | 3 | 3 | 3 |
| 39 | 3 | 1 | 3 |
| 40 | 3 | 3 | 3 |
| 42 | 3 | 3 | 3 |
| 43 | 3 | 2 | 3 |
| 46 | 3 | 1 | 3 |
| 47 | 3 | 3 | 3 |
| 49 | 3 | 2 | 3 |
| 50 | 3 | 3 | 3 |
| 51 | 3 | 3 | 3 |
| 52 | 3 | 3 | 3 |

C.4 Synergistic effect in combinations with BIT

Biocidal activity against bacterial/yeast growth was determined with the poison plate assay. To obtain the required concentrations of the test compound, calculated amounts of stock solutions (DMSO) were pipetted into multi-well plates. Tryptose agar (except for Rhodotorula: PDA) was added aseptically and uniform distribution was obtained by shaking. Each plate was inoculated with a bacterial/yeast suspension. After incubation at 27° C. and 70% relative humidity, for a period long enough to allow complete growth of controls, percentage activity as compared to the control was scored.

Possible synergy was investigated using Limpel's formula (Richter, D. L., *Pestic. Sci.* 1987, 19: 309–315):

$$E_c = X + Y - \frac{X \cdot Y}{100}$$

where $E_C$ is the expected additive response, or calculated activity, X is the observed percentage control when compound A is applied alone and Y is the observed percentage control when compound B is applied alone. Synergy was considered to occur when the observed effect, or measured activity, of a combination of both compounds was greater than the corresponding $E_C$ value.

The table C.4 to C.6 below enumerate the measured and calculated activities of BIT and compounds 20, 42 and 40 when tested as a single test compound or as a combination against *Rhodotorula rubra* or *Cellulomonas flavigena*. BIT (1,2-benzisothiazol-3(2H)-one) is a well-known bacteride and was tested at a concentration of 25 and 50 μmol. Compounds 20, 40 and 42 were tested at a concentration of 25, 50 and 75 μmol. When a synergistic effect was observed, the "measured" and "calculated" activity are indicated with a bold typeface.

TABLE C.4

Percentage activity of BIT, compound 20 and their combination (concentration of BIT and Co. No. 20 expressed in μmol)

| BIT | Co. No. 20 | Measured activity | Calculated activity |
|---|---|---|---|
| *Rhodotorula rubra* | | | |
| 0 | 0 | 0 | |
| 25 | 0 | 0 | |
| 50 | 0 | 0 | |
| 0 | 25 | 0 | |
| 0 | 50 | 0 | |
| 0 | 75 | 0 | |
| 25 | 25 | 0 | 0 |
| 25 | 50 | 100 | 0 |
| 25 | 75 | 100 | 0 |
| 50 | 25 | 100 | 0 |
| 50 | 50 | 100 | 0 |
| 50 | 75 | 100 | 0 |
| *Cellulomonas flavigena* | | | |
| 0 | 0 | 0 | |
| 25 | 0 | 0 | |
| 50 | 0 | 100 | |
| 0 | 25 | 0 | |
| 0 | 50 | 0 | |
| 0 | 75 | 0 | |
| 25 | 25 | 0 | 0 |
| 25 | 50 | 100 | 0 |
| 25 | 75 | 95 | 0 |
| 50 | 25 | 100 | 100 |
| 50 | 50 | 100 | 100 |
| 50 | 75 | 100 | 100 |

TABLE C.5

Percentage activity of BIT, compound 42 and their combination (concentration of BIT and Co. No. 42 expressed in μmol)

| BIT | Co. No. 42 | Measured activity | Calculated activity |
|---|---|---|---|
| *Rhodotorula rubra* | | | |
| 0 | 0 | 0 | |
| 25 | 0 | 0 | |
| 50 | 0 | 0 | |
| 0 | 25 | 0 | |
| 0 | 50 | 0 | |
| 0 | 75 | 0 | |
| 25 | 25 | 0 | 0 |
| 25 | 50 | 90 | 0 |
| 25 | 75 | 100 | 0 |
| 50 | 25 | 100 | 0 |
| 50 | 50 | 100 | 0 |
| 50 | 75 | 100 | 0 |
| *Cellulomonas flavigena* | | | |
| 0 | 0 | 0 | |
| 25 | 0 | 0 | |
| 50 | 0 | 100 | |
| 0 | 25 | 0 | |
| 0 | 50 | 0 | |
| 0 | 75 | 0 | |
| 25 | 25 | 100 | 0 |
| 25 | 50 | 100 | 0 |
| 25 | 75 | 100 | 0 |
| 50 | 25 | 100 | 100 |
| 50 | 50 | 100 | 100 |
| 50 | 75 | 100 | 100 |

TABLE C.6

Percentage activity of BIT, compound 40 and their combination (concentration of BIT and Co. No. 40 expressed in μmol)

| BIT | Co. No. 40 | Measured activity | Calculated activity |
|---|---|---|---|
| *Rhodotorula rubra* | | | |
| 0 | 0 | | |
| 25 | 0 | 0 | |
| 50 | 0 | 0 | |
| 0 | 25 | 90 | |
| 0 | 50 | 100 | |
| 0 | 75 | 100 | |
| 25 | 25 | 100 | 90 |
| 25 | 50 | 100 | 100 |
| 25 | 75 | 100 | 100 |
| 50 | 25 | 100 | 90 |
| 50 | 50 | 100 | 100 |
| 50 | 75 | 100 | 100 |
| *Cellulomonas flavigena* | | | |
| 0 | 0 | 0 | |
| 25 | 0 | 0 | |
| 50 | 0 | 100 | |
| 0 | 25 | 0 | |
| 0 | 50 | 0 | |
| 0 | 75 | 0 | |
| 25 | 25 | 100 | 100 |
| 25 | 50 | 100 | 100 |
| 25 | 75 | 100 | 100 |
| 50 | 25 | 100 | 100 |
| 50 | 50 | 100 | 100 |
| 50 | 75 | 100 | 100 |

The table C.7 to C.8 below enumerate the measured and calculated activities of BAC and compounds 20, 42 and 40 when tested as a single test compound or as a combination against *Providencia rettgeri*. BAC (benzalconium chloride) is a well-bacteride and was tested at a concentration of 40 and 80 μmol. Compounds 20, 40 and 42 were tested at a concentration of 10, 20, 40, 80 and 160 μmol. When a synergistic effect was observed, the "measured" and "calculated" activity are indicated with a bold typeface.

TABLE C.7

Percentage activity of BAC, compound 20 or compound 40 and their combination (concentration of BAC and Co. No. 20 or 40 expressed in μmol)

| | *Providencia rettgeri* | | | | *Providencia rettgeri* | |
|---|---|---|---|---|---|---|
| BAC | Co. No. 20 | Measured activity | Calculated activity | BAC | Co. No. 40 | Measured activity | Calculated activity |
| 0 | 0 | 0 | | 0 | 0 | 0 | |
| 40 | 0 | 0 | | 40 | 0 | 50 | |
| 80 | 0 | 100 | | 80 | 0 | 100 | |
| 0 | 10 | 0 | | 0 | 10 | 0 | |
| 0 | 20 | 0 | | 0 | 20 | 0 | |
| 0 | 40 | 30 | | 0 | 40 | 90 | |
| 0 | 80 | 90 | | 0 | 80 | 100 | |
| 0 | 160 | 100 | | 0 | 160 | 100 | |
| 40 | 10 | 50 | 0 | 40 | 10 | 100 | 50 |
| 40 | 20 | 50 | 0 | 40 | 20 | 100 | 50 |
| 40 | 40 | 100 | 30 | 40 | 40 | 100 | 95 |
| 40 | 80 | 100 | 90 | 40 | 80 | 100 | 100 |
| 40 | 160 | 100 | 100 | 40 | 160 | 100 | 100 |
| 80 | 10 | 100 | 100 | 80 | 10 | 100 | 100 |
| 80 | 20 | 100 | 100 | 80 | 20 | 100 | 100 |
| 80 | 40 | 100 | 100 | 80 | 40 | 100 | 100 |
| 80 | 80 | 100 | 100 | 80 | 80 | 100 | 100 |
| 80 | 160 | 100 | 100 | 80 | 160 | 100 | 100 |

TABLE C.8

Percentage activity of BAC, compound 42 and their combination (concentration of BAC and Co. No. 42 expressed in μmol).
*Providencia rettgeri*

| BAC | Co. No. 42 | Measured activity | Calculated activity |
|---|---|---|---|
| 0 | 0 | 0 | |
| 40 | 0 | 0 | |
| 80 | 0 | 100 | |
| 0 | 10 | 0 | |
| 0 | 20 | 0 | |
| 0 | 40 | 30 | |
| 0 | 80 | 90 | |
| 0 | 160 | 100 | |
| 40 | 10 | 50 | 0 |
| 40 | 20 | 50 | 0 |
| 40 | 40 | 100 | 30 |
| 40 | 80 | 100 | 90 |
| 40 | 160 | 100 | 100 |
| 80 | 10 | 100 | 100 |
| 80 | 20 | 100 | 100 |
| 80 | 40 | 100 | 100 |
| 80 | 80 | 100 | 100 |
| 80 | 160 | 100 | 100 |

What is claimed is:

1. A compound of formula (I)

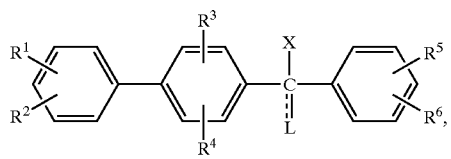

(I)

a stereochemically isomeric form thereof, an acid or base addition salt thereof, an N-oxide thereof, or a quaternary ammonium derivative thereof,
wherein
the dotted line is an optional bond;

X is a direct bond when the dotted line represents a bond, or

X is hydrogen or hydroxy, when the dotted line does not represent a bond;

$R^1$ and $R^2$ are each independently selected from hydrogen, halo, hydroxy, $C_{1-4}$alkyl, $C_{1-4}$alkyloxy, nitro, amino, cyano, trifluoromethyl, trifluoromethoxy, $C_{1-6}$alkylcarbonyl, hydroxycarbonyl, $C_{1-6}$alkyloxycarbonyl, aminocarbonyl, di($C_{1-4}$alkyl)aminocarbonyl, $C_{1-6}$alkylsulfinyl, $C_{1-6}$alkylsulfonyl, aminosulfonyl, di($C_{1-4}$alkyl)aminosulfonyl, or —$SO_3H$;

$R^3$ and $R^4$ are each independently selected from hydrogen, halo, hydroxy, $C_{1-4}$alkyl, $C_{1-4}$alkyloxy, nitro, amino, cyano, trifluoromethyl, or trifluoromethoxy;

$R^5$ and $R^6$ are each independently selected from hydrogen, halo, hydroxy, $C_{1-4}$alkyl, $C_{1-4}$alkyloxy, nitro, amino, cyano, trifluoromethyl, trifluoromethoxy, $C_{1-6}$alkylcarbonyl, hydroxycarbonyl, $C_{1-6}$alkyloxycarbonyl, aminocarbonyl, di($C_{1-4}$alkyl)aminocarbonyl, $C_{1-6}$alkylsulfinyl, $C_{1-6}$alkylsulfonyl, aminosulfonyl, di($C_{1-4}$alkyl)aminosulfonyl, or —$SO_3H$, ====L is a radical of formula

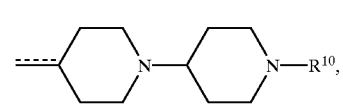

(a-1)

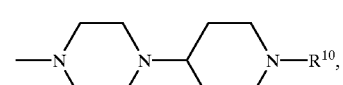

(a-2)

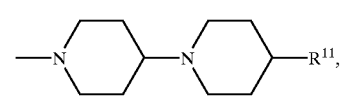

(a-3)

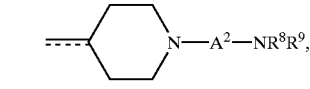

(a-4)

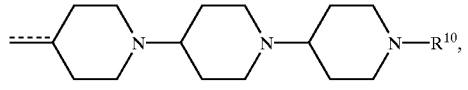

(a-5)

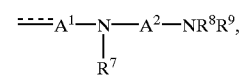

(a-6)

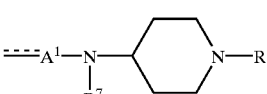

(a-7)

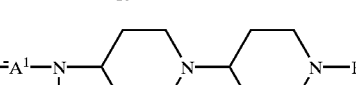

(a-8)

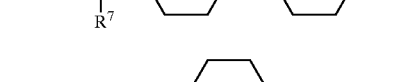

(a-9)

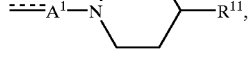

-continued

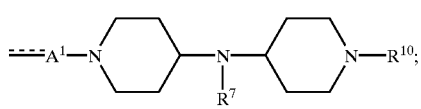

(a-10)

wherein
$A^1$ is a direct bond or $C_{1-6}$alkanediyl;
$A^2$ is $C_{2-6}$alkanediyl;
$R^7$ is hydrogen, $C_{1-4}$alkyl, phenyl or benzyl;
$R^8$ and $R^9$ are each independently hydrogen, $C_{1-6}$alkyl, amino$C_{1-6}$alkyl or mono- or di($C_{1-4}$alkyl)amino$C_{1-6}$alkyl;
$R^{10}$ is hydrogen, $C_{1-6}$alkyl, amino$C_{1-6}$alkyl or mono- or di($C_{1-4}$alkyl)amino$C_{1-6}$alkyl; and
$R^{11}$ is hydrogen, $C_{1-6}$alkyl, amino, amino$C_{1-6}$alkyl or mono- or di($C_{1-4}$alkyl)amino$C_{1-6}$alkyl;
provided that when L is a radical of formula (a-9) then R11 is other than hydrogen.

2. A compound as claimed in claim 1 wherein L is a radical of formula (a-1), (a-2), (a-3), (a-5), (a-7), (a-8), or (a-10), wherein $R^{10}$ is hydrogen, $C_{1-6}$alkyl, or di($C_{1-4}$alkyl)amino$C_{1-6}$alkyl.

3. A compound as claimed in claim 1 wherein L is a radical of formula (a-3) or (a-9) wherein $R^{11}$ is hydrogen, $C_{1-6}$alkyl, amino, amino$C_{1-6}$alkyl or di($C_{1-4}$alkyl)amino-$C_{1-6}$alkyl.

4. A compound as claimed in claim 1 wherein wherein L is a radical of formula (a-4) or (a-6) wherein $R^8$ and $R^9$ are each independently hydrogen, $C_{1-4}$alkyl, or amino$C_{1-6}$alkyl.

5. A compound as claimed in claim 1 wherein the compound is
4-[[(1,1'-biphenyl)-4-yl]phenylmethyl](1,4'-bipiperidine),
4-[[(1,1'-biphenyl)-4-yl]phenylmethyl]-1-piperidinepropanamine,
N-[3-[(1,1'-biphenyl)-4-yl]-3-phenylpropyl]-1,3-propanediamine, and
the acid or base addition salts, the stereoisomeric forms, the N-oxides, or quaternary ammonium derivatives thereof.

6. A compound as claimed in claim 5 wherein the acid addition salts are 1,2-benzisothiazolone (BIT) salts.

7. A biocidal composition comprising one or more inert carriers and, if desired, other adjuvants, and as active ingredient a biocidally effective amount of a compound as claimed in claim 1.

8. A biocidal composition as claimed in claim 7 further comprising one or more other active ingredients selected from bactericides, fungicides, insecticides, acaricides, nematicides, and herbicides.

9. A method of controlling micro-organisms by the application of one or more compounds as claimed in claim 1 to said micro-organisms.

10. A composition comprising a compound as claimed in claim 1, and another active ingredient, in quantities producing a biocidal synergistic effect, and a carrier.

11. A composition according to claim 10 wherein the other active ingredient is a fungicide or a bactericide.

12. A process for preparing a compound of formula (I) wherein
a) an organometallic derivative of an intermediate of formula (II), wherein halo' represents chloro, bromo or iodo, is reacted with an intermediate of formula (III), yielding compounds of formula (I-a), defined as compounds of formula (I) wherein X is hydroxy and the dotted line does not represent a bond;

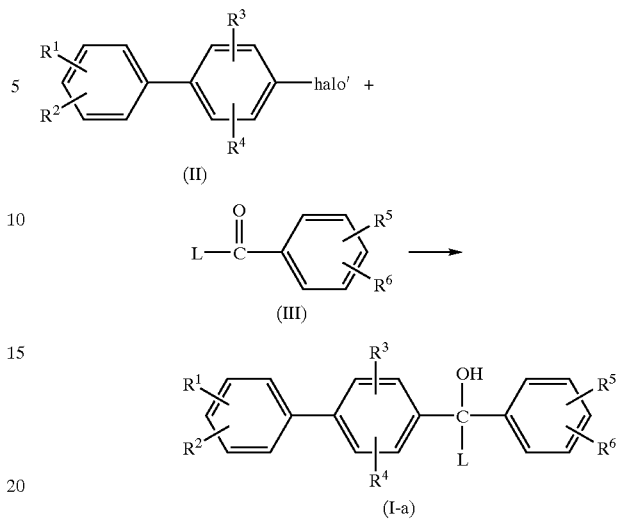

b) an intermediate of formula (V) is N-alkylated with an intermediate of formula (IV) in a reaction-inert solvent and, optionally in the presence of a suitable base, yielding compounds of formula (I-c-1), defined as compounds of formula (I) wherein X is hydrogen and the dotted line does not represent a bond and $L^1$ represents a radical of formula (a-2), (a-3), (a-6) to (a-10) wherein $A^1$ is a direct bond;

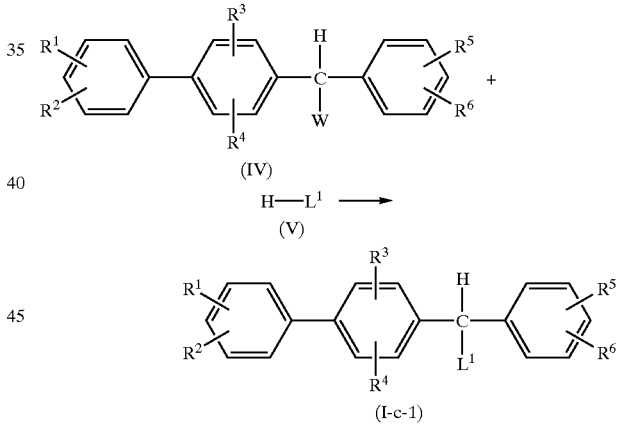

c) an intermediate of formula (VI) is reacted with an intermediate of formula (VII) in a reaction-inert solvent, yielding compounds of formula (I-d), defined as compounds of formula (I) wherein $L^2$ represents a radical of formula (a-6) to (a-10) wherein $A^1$ is $C_{1-6}$alkanediyl;

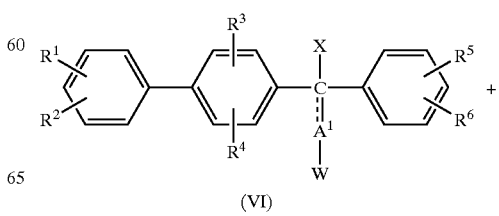

(VII) → 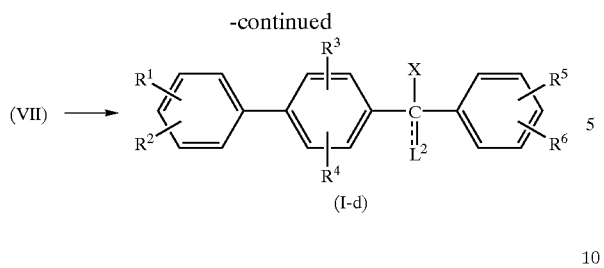

(I-d)

said intermediate of formula (VII) has one of the following structures:

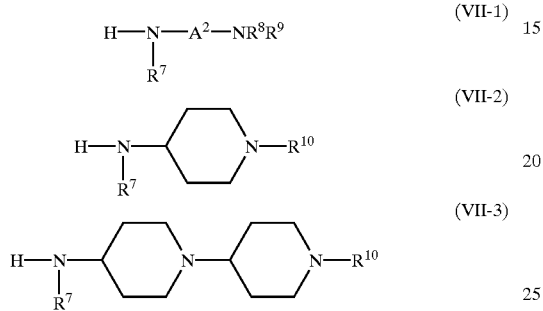

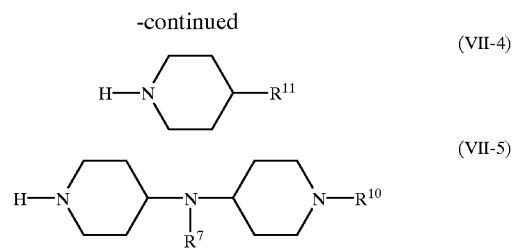

wherein in the above reaction schemes the radicals L, $R^1$ to $R^{10}$ are as defined in claim 1 and W is an appropriate leaving group;

d) or, compounds of formula (I) are converted into each other following art-known transformation reactions; or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

\* \* \* \* \*